United States Patent
Shnaiderman et al.

(10) Patent No.: US 12,076,116 B2
(45) Date of Patent: Sep. 3, 2024

(54) SENSOR FOR TISSUE MEASUREMENTS

(71) Applicant: TECHNISCHE UNIVERSITÄT MÜNCHEN, Munich (DE)

(72) Inventors: Rami Shnaiderman, Munich (DE); Georg Michael Wissmeyer, Munich (DE); Vasilis Ntziachristos, Gräfelfing (DE)

(73) Assignee: TECHNISCHE UNIVERSITÄT MÜNCHEN, Munich (DE)

( * ) Notice: Subject to any disclaimer, the term of this patent is extended or adjusted under 35 U.S.C. 154(b) by 882 days.

(21) Appl. No.: 16/979,028

(22) PCT Filed: Mar. 6, 2019

(86) PCT No.: PCT/EP2019/055519
§ 371 (c)(1),
(2) Date: Sep. 8, 2020

(87) PCT Pub. No.: WO2019/170176
PCT Pub. Date: Sep. 12, 2019

(65) Prior Publication Data
US 2021/0052164 A1 Feb. 25, 2021

(30) Foreign Application Priority Data

Mar. 9, 2018 (EP) .................... 18160940

(51) Int. Cl.
*A61B 5/00* (2006.01)
*A61B 5/02* (2006.01)
*A61B 5/145* (2006.01)

(52) U.S. Cl.
CPC ........ *A61B 5/0095* (2013.01); *A61B 5/02007* (2013.01); *A61B 5/14542* (2013.01); *A61B 5/443* (2013.01); *A61B 5/7257* (2013.01)

(58) Field of Classification Search
None
See application file for complete search history.

(56) References Cited

U.S. PATENT DOCUMENTS

| | | | |
|---|---|---|---|
| 5,840,023 A | 11/1998 | Oraevsky et al. | |
| 6,049,728 A | 4/2000 | Chou | |
| 6,466,806 B1 | 10/2002 | Geva et al. | |
| 7,515,948 B1 | 4/2009 | Balberg et al. | |
| 9,351,705 B2 * | 5/2016 | Wang | A61B 8/4461 |
| 2005/0054906 A1 | 3/2005 | Page et al. | |

(Continued)

FOREIGN PATENT DOCUMENTS

| | | |
|---|---|---|
| GB | 2 322 941 | 9/1998 |
| JP | S 61-238236 A | 10/1986 |

(Continued)

OTHER PUBLICATIONS

International Search Report and Written Opinion for PCT Application No. PCT/EP2019/055519 mailed Apr. 3, 2019.

(Continued)

*Primary Examiner* — Ankit D Tejani
(74) *Attorney, Agent, or Firm* — Branch Partners PLLC; Bruce E. Black

(57) ABSTRACT

The present invention relates to a sensor for non-invasive optoacoustic measurements of biomechanical and/or morphological features of skin and/or other tissue.

27 Claims, 7 Drawing Sheets

(56) References Cited

U.S. PATENT DOCUMENTS

Figure 1B:
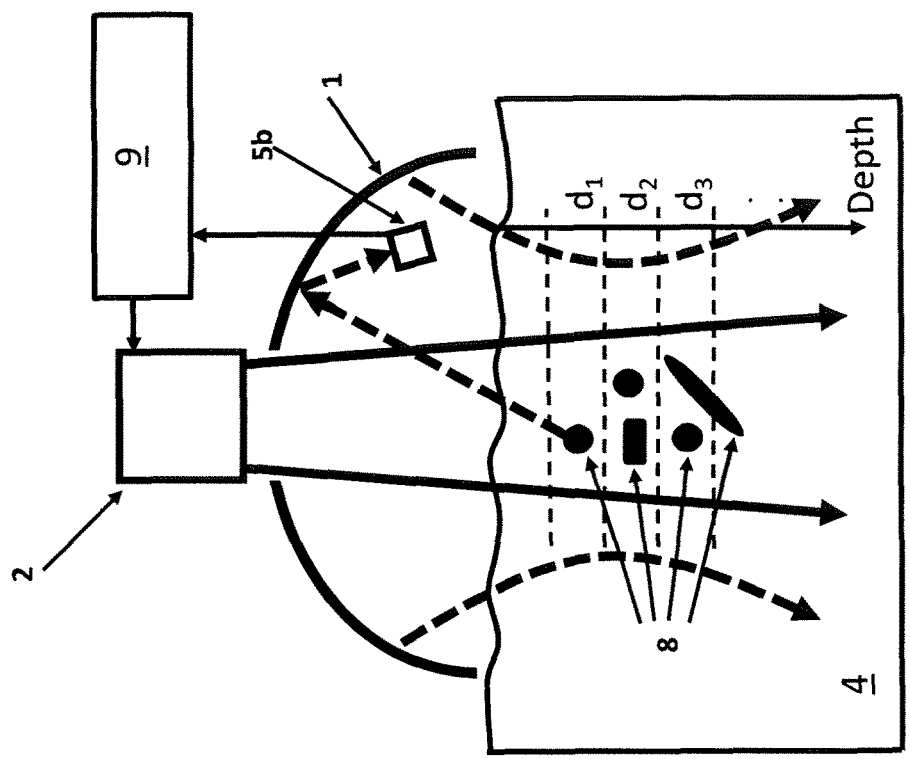

| | | | |
|---|---|---|---|
| 2007/0179365 A1 | 8/2007 | Bitton et al. | |
| 2008/0255433 A1* | 10/2008 | Prough | A61B 5/0095 |
| | | | 600/301 |
| 2011/0275890 A1 | 11/2011 | Wang et al. | |
| 2012/0029829 A1 | 2/2012 | Li et al. | |
| 2012/0123256 A1 | 5/2012 | Razansky et al. | |
| 2013/0123590 A1 | 5/2013 | Naganuma et al. | |
| 2013/0190591 A1 | 7/2013 | Hirson et al. | |
| 2014/0049770 A1 | 2/2014 | Li et al. | |
| 2014/0163353 A1 | 6/2014 | Razansky et al. | |
| 2015/0038813 A1 | 2/2015 | Kawaguchi et al. | |
| 2015/0101411 A1 | 4/2015 | Zalev et al. | |

FOREIGN PATENT DOCUMENTS

| | | |
|---|---|---|
| JP | 2010139510 | 6/2010 |
| JP | 2012135368 | 7/2012 |
| JP | 2013027522 | 2/2013 |
| WO | WO2011000389 | 1/2011 |
| WO | 2017/222033 | 12/2017 |

OTHER PUBLICATIONS

Extended European Search Report for EP Patent Application No. 18160940.5 mailed Aug. 29, 2018.

M. Omar et al., Pushing the Optical Imaging Limits of Cancer with Multi-Frequency-Band Raster-Scan Optoacoustic Mesoscopy (RSOM), Neoplasis, vol. 17, No. 2, pp. 208-214, 2015.

M. Schwarz et al., Three-dimensional multispectral optoacoustic mesoscopy reveals melanin and blood oxygenation in human skin in vivo, J. Biophotonics, vol. 9, No. 1-2, pp. 55-60, 2016.

Schwarz et al. Motion correction in optoacoustic mesoscopy. Sci Rep. 2017; 7: 10386. doi: 10.1038/s41598-017-11277-y.

Jürgen Glatz, Nikolaos C. Deliolanis, Andreas Buehler, Daniel Razansky, and Vasilis Ntziachristos, "Blind source unmixing in multi-spectral optoacoustic tomography," Opt. Express 19, 3175-3184 (2011).

Choi SS, Mandelis A, Guo X, Lashkari B, Kellnberger S, Ntziachristos V. Wavelength-Modulated Differential Photoacoustic Spectroscopy (WM-DPAS) for noninvasive early cancer detection and tissue hypoxia monitoring. J Biophotonics. Apr. 2016;9(4):388-95. doi: 10.1002/jbio.201500131. Epub May 21, 2015. PMID: 25996635.

* cited by examiner

SENSOR FOR TISSUE MEASUREMENTS

CROSS-REFERENCE TO RELATED APPLICATIONS

This present application is a U.S. national stage application of PCT Application No. PCT/EP2019/055519, filed Mar. 6, 2019, which claims priority to European Patent Application No. 18160940.5 filed Mar. 9, 2018, both of which are hereby incorporated by reference in their entirety.

The present invention relates to a sensor for non-invasive optoacoustic measurements of features of skin and/or other tissue, in particular of biochemical, (patho-)physiological, cellular, subcellular or morphological features and constituents of skin and/or other tissue.

Many studies have identified that changes in skin characteristics, including microvasculature are an early indicator of cardiovascular disease and diabetes. The skin is generally considered a "window" to many diseases and it can allow monitoring of a number of parameters, from skin components to moieties circulating in the blood stream. More generally, sensing of tissues, such as skin and tissues situated under the skin including muscle or fat deposits can play an important role in reducing cost and improving quality of healthcare by delivering early warning or detection of various conditions including physiology, pathophysiology and disease or monitoring disease progression and treatment efficacy. Warning in this case refers to a process that detects and informs on physiological conditions and alterations, disease onset, disease progression, treatment efficacy and so on. These abilities apply to both point-of-care (short-term) and home-monitoring (long-term) applications for a high-risk population (e.g. obese, metabolic syndrome, hypertensive). More generally, these abilities apply to the health conscious individual and medical doctor wishing to monitor several parameters of body function, monitor or understand food-intake and metabolism or aspects of disease, such as cardiovascular disease or diabetes. One technology suitable for identifying such changes in skin and other tissues utilizes optoacoustic measurements. Optoacoustics allows for dis-entangling scattering from absorption and for resolving depth. It is thus possible to measure unique tissue optical features with optoacoustics, which was not possible with previous technologies such as Diffuse Optical Spectroscopy. Optoacoustics also allows for significantly higher accuracy than Diffuse Optical Spectroscopy.

The use of optoacoustic or photoacoustic measurements is already known for the purpose of medical diagnosis (see, e.g., US 2015/0038813, U.S. Pat. No. 5,840,023, US 2007/0179365, U.S. Pat. Nos. 6,466,806 and 6,049,728). However, previous optoacoustic or photoacoustic measurements for diagnosis were based on optoacoustic or photoacoustic imaging techniques. Yet, such imaging techniques are far too complex and much too expensive for a simple monitor envisaged to monitor, e.g., changes in skin or other tissues for example as an early indicator of cardiovascular disease and/or diabetes.

It is thus an object of the present invention to provide an improved sensor for non-invasive optoacoustic measurements of skin and other tissues, which is simple and cost effective. This object is achieved with a sensor according to claim 1.

Accordingly, the present invention relates to a sensor for non-invasive optoacoustic measurements of skin and tissue constituents and features, including morphological, physiological and molecular features, in skin and tissue or moieties circulating in the vasculature or distributed within the tissue interrogated. The sensor comprises a casing adapted and configured to be attached to the epidermis of a person, a light source adapted and configured to simultaneously illuminate an illumination volume of the person's skin tissue once the casing is attached to the epidermis of the person, and one or more ultrasound detectors adapted and configured to detect an ultrasound signal emitted from a common detection volume of the person's skin tissue once the casing is attached to the epidermis of the person. The intersection between the illumination volume and the common detection volume defines an interrogation volume which remains fixed (i.e. stationary and constant in size and volume) once the casing is attached to the epidermis of the person. It is to be understood that while skin is a preferred application, the sensor can be applied to any tissue application, including endothelial tissues and overall exposed internal tissues for example as part of an interventional procedure, including endoscopy or surgery.

In contrast to imaging techniques according to the prior art, the sensor of the present invention defines a new sensor class yielding unique non-invasive measurements, i.e. measurements without disruption of the interface of the tissue measured. According to preferred features herein, the measurements can be microvascular, (patho-)physiological, cellular, molecular or constituents in tissue, including circulating moieties in the vascular system detected over depth, using single-point, preferably broadband, optoacoustic detection. The invention is, inter alia, based on the idea to gather all information from a single interrogation volume (defined by the intersection between the illumination volume and the single common detection volume of the one or more ultrasound detectors), which remains stationary during detection, i.e. during the non-invasive optoacoustic measurement, and to extract features of the tissue within said interrogation volume by analyzing the information collected from said single interrogation volume. Since the illumination volume is illuminated simultaneously and since the interrogation volume remains fixed once the casing is attached to the epidermis of the person, the sensor according to the present invention eliminates the need for scanning and, in particular, for any moving parts within the sensor. This allows for a much simpler and less costly technical implementation than prior imaging devices, because the light source and the one or more ultrasound detectors preferably remain stationary with respect to each other during detection and, accordingly, can be implemented as immovable parts within the sensor casing.

In the context of the present invention, the illumination volume is defined as the volume comprising all points in space where the intensity of illumination corresponds to at least 50% of the maximum illumination.

In the context of the present invention, the detection volume is defined as the volume comprising all points in space where the sensitivity of the one or more ultrasound detectors corresponds to at least 50% of the maximum sensitivity.

The sensor is preferably adapted and configured to collect data from the entire interrogation volume and to discriminate data originating from subsections of the interrogation volume having different distances from the one or more ultrasound detectors. This discrimination is preferably possible without any scanning and without changing the focus of either the light source or the one or more ultrasound detectors. Rather, the discrimination is performed by data analysis such as analysis of the time or phase of sound propagation. The subsections of the interrogation volume may have different shapes, which are preferably defined by the number, detection characteristics and arrangement of the one or more ultrasound detectors. For example, in case of a single point-like detector, the subsections may have the shape of spherical shells. If, however, several ultrasound detectors are arranged in a planar configuration, the subsections may have the shape of planar sheets being substantially parallel to the epidermis. Establishment of planar sheets can also be achieved by appropriately manufactured detectors, for example single element detectors with an extended detection area, elongated along at least one dimension. For example, using a single element line detector measuring, e.g., 5 mm in length, or using a detector array such as a linear array, an axicon or an annular detector/annular detector array but utilizing all measurements from each different element to provide a measurement as if it is produced by a single element detector allows for data generation in well-defined planar sheets. For example, signals from the different elements can be delayed and summed, averaged, subtracted or undergo similar operations, however yielding for the purposes of the inventive sensor herein one measurement in analogy to utilizing a single element detector. In other words, if more than one ultrasound detector is utilized, the common detection volume is defined by the merging parts of the detection volumes of all ultrasound detectors. For example a common detection volume (CDV) collected by two focused ultrasound detectors can be defined as the volume that is covered by both detectors in a sense of an "AND" Boolean operation, i.e. all volume belonging to volumes sampled by both detectors constitutes the CDV and all volumes that are not covered by at least one detector are not part of the common detection volume. This "AND" operation can be achieved by time-gating the optoacoustic signals collected and appropriately recording only signals collected from the common detection volume. By changing the geometry of the detectors (detection area, placement in relation to the illumination unit and sensor casing) a different CDV can be defined. However, the inventive sensor does not discriminate between the detection volumes of individual ultrasound detectors, i.e. volumes that are not part of the CDV. Rather, the ultrasound signal from the entire CDV is detected and analyzed as a single measurement. Nevertheless, this collection practice is in contradistinction of imaging systems, where information is collected from volumes covered by individual detectors and not only the CDV, which is only the volume corresponding to the overlap or "volumetric cross-section" of the volumes covered by individual detectors.

The measurement obtained from the CDV is a measurement along depth or distance from the detector or zero geometrical point, i.e. a measurement along one single geometrical dimension. As explained in the following, by further timing signals from the CDV, one can collect sub-volumes or layers from within the CDV. Discrimination between spatial subsections within the CDV is performed by analysis along one direction only, commonly the depth direction. In other words, the spatial subsections correspond to layers in relation to a well-defined geometrical reference point. In case of a single point-like detector, the layers may have the shape of spherical shells, whereas the layers may be planar or also curved in case of a detector array.

The sensor of the present invention is preferably adapted and configured to analyze data along a single geometrical dimension, which preferably corresponds to depth. This is contrary to common imaging techniques which typically allow for analysis of at least two geometrical dimensions (i.e., the generation of a 2D-image) or even three geometrical dimensions (i.e. the generation of a 3D-image). In other words, the sensor of the present invention is preferably adapted and configured to discriminate between different layers, for example along depth, but not to discriminate volumes along a second or a third geometrical dimension. This further distinguishes the present invention over common imaging techniques which allow for discrimination of sub-volumes (voxels) along at least two or three geometrical dimensions in order to generate an image. This is, e.g., possible due to a reconstruction approach called inversion. During the inversion processes utilized in imaging applications, data collected from different volumes are mathematically combined in a two-dimensional or three-dimensional fashion in order to generate a 2D or 3D image respectively. Yet, this information or process is not required in the present invention which aims at qualitative and quantitative information at different depths. Therefore, the sensor of the present invention does not utilize inversion. Likewise, the sensor of the present invention does not utilize signals from multiple detectors if these signals do not come from the same CDV. In other words, all signals that do not correspond to the CDV are rejected by the inventive sensor and not utilized in computations.

The sensor is adapted and configured to analyze data originating from the entire interrogation volume or preferably from one or more specific subsections of the interrogation volume having different distances from the one or more ultrasound detectors and to extract features of the skin or other tissues at different depths. Since the present invention, inter alia, utilizes integration, bandwidth analysis and other inventive features disclosed in the following, it is not necessary to resolve information in the x-y-plane perpendicular to the depth direction.

Yet, it is advantageous to provide information for different depths as this may be physiologically relevant. It is thus preferred that the sensor of the present invention provides features of the skin or other tissues at different depths, wherein the extracted information relating to a specific depth is extracted from the entire subsection corresponding to one depth (as noted above, the term "depth" may not correspond to the actual depth but may also, depending on the shape of the subsection, correspond, e.g., to the radius of the spherical shell of the subsection).

Preferably, the interrogation volume has a size of at least 500.000 µm$^3$, preferably of at least 0.001 mm$^3$, more preferably of at least 0.002 mm$^3$, even more preferably of at least 0.004 mm$^3$ and most preferably of at least 0.01 mm$^3$. Preferably, the casing comprises a, preferably flat, sensing surface adapted and configured to be attached to the epidermis of a person and wherein the interrogation volume has a maximum cross section substantially parallel to said sensing surface being at least 7.500 µm$^2$, preferably at least 15.000 µm$^2$, more preferably at least 30.000 µm$^2$ and most preferably at least 60.000 µm$^2$. Preferably, the casing comprises a, preferably flat, sensing surface adapted and configured to be attached to the epidermis of a person and wherein the interrogation volume has a maximum extension substantially perpendicular to said sensing surface being at least 100 µm, preferably at least 200 µm, more preferably at least 300 µm and most preferably at least 500 µm.

The sensor preferably utilizes at least one illumination path to excite tissue within the illumination volume at least one wavelength. The illumination excites optoacoustic responses from the illumination volume using photons that scatter and possibly diffuse through tissue. Preferably, the sensor illuminates the tissue at more than one wavelength. For example, wavelengths in the visible (e.g. 515 nm, 532 nm) allow measurements of vascularization and blood oxygenation parameters. Wavelengths above 900 nm, for example 930 nm or 1210 nm enable lipid and/or water measurements. A single wavelength can be sensitive preferentially to a tissue constituent (e.g. hemoglobin or lipid) or influenced by multiple tissue constituents. Separation of constituents may require spectral separation techniques, ranging from simple subtraction methods to linear or non-linear spectral unmixing techniques. Preferably, ratiometric methods, i.e. the division of measurements in one wavelength by measurements at a different wavelength, obtained from the same volume, may be utilized to allow accurate determination of skin or other tissue parameters, including tissue oxygenation or fat to water ratio.

The one or more ultrasound detectors can comprise any ultrasound detector suitable for optoacoustic measurement and may comprise one or a combination of: PZT, CMUT, LiNBO3, fiber-interferometry or optical refractometer. The light emitted from the light source can preferably be transmitted through the ultrasound detector. This can, e.g., be achieved by an optically transparent detector or by a detector with an opening for an optical path. Alternatively or in addition, the light emitted from the light source can pass at least one side of the ultrasound detector. A further alternative implementation places multiple ultrasound detectors around the optical source, optical port or optical path, as to effectively generate light passing through an ultrasound detection area.

As mentioned above, the one or more ultrasound detectors (or detector elements) preferably detect an ultrasound signal originating from a common detection volume, preferably from a single detection volume. The interrogation volume of the sensor is defined by the intersection of illumination volume and the detection volume detected by the one or more ultrasound detectors (i.e., the volume of view of the ultrasound detectors). The one or more ultrasound detectors may comprise multiple detector elements, including elements arranged in concentric rings (annular detector). However, compared to an imaging system, one preferred characteristic of the sensor is that all detector elements collect information from a single interrogation volume. Therefore, the possible use of an ultrasound detector with multiple detector elements is preferred for better defining the volume of view through ultrasound focusing mechanisms and improving the signal to noise ratio of the detected signal. We note that each of the elements may cover the same or a slightly different volume, which may overlap with the volume covered by an adjacent detector. Nevertheless, the sensor, in its basic operation, collects and reports measurements from one interrogation volume consisting of the superposition of these volumes. In other words, the interrogation volume of the sensor is an average of all the individual volumes examined by the different detectors and therefore the reported measurements are a combination of the measurements recorded by each individual detector. Nevertheless, for cost reduction purposes, it is preferred that sensors are constructed with one detection element.

At least one ultrasound focusing element (e.g., sound lenses) can be employed for better defining the detection volume and, consequently, the interrogation volume. Optical focusing elements and other optical components (e.g., mirrors, lenses, fibers, etc.) and operations may be also employed for adjusting the illumination characteristics, for example for defining the illumination volume, the illumination area on the skin surface, tuning the illumination angle, etc.

The one or more ultrasound detectors are preferably of broadband nature. Preferably, the one or more ultrasound detectors are broadband detectors adapted and configured to detect ultrasound over a frequency band of at least 30 MHz, preferably at least 50 MHz, more preferably at least 70 MHz. Preferably, the one or more ultrasound detectors are broadband detectors adapted and configured to detect ultrasound over a frequency band covering at least 20-40 MHz, preferably at least 15-60 MHz, more preferably at least 10-80 MHz. Bandwidth may play an important role in the operation of the sensor. The broader the bandwidth, the more detailed the information that is collected from the volume interrogated. The useful bandwidth is determined by depth, i.e. propagation-distance-dependent ultrasound attenuation. Nevertheless, for sensors operating with superficial interrogation volumes, for example reaching depths of only 1-2 mm, bandwidths of 200 MHz (e.g. 10-210 Mhz) or broader contain diagnostic or otherwise important information. For deeper volumes, the upper bandwidth frequencies may drop to a few tens of MHz or less.

The casing or encasing of the sensors preferably contains and transports optical, ultrasound and electrical signals. Typically, at least electrical signals are communicated in and out of the encasing. However, all optical, electrical and ultrasound signals are present within the encasing for any given measurement. The ultrasound and optical signals may be present only on the interface of the sensor but within the encasing as defined by the, preferably rigid, structure and interface. However, in case of sensors utilizing cavities for signal amplification, the optical and ultrasound signals may occupy and propagate over a larger volume within the encasing.

The sensor may have light delivered from the outside into the encasing and eventually to tissue through an optical path and port. However the light can be generated also within the encasing using an optical source, such as at least one light emitting diode, laser diode or similar light generating component. Thus, the light source of the present invention may be an active light source actually generating light or a passive light source such as a light guide or the like which may be supplied with optical illumination through an optical port.

The light source preferably comprises a laser and/or an LED. Preferably, the light source is an intensity modulated light source or a pulsed light source. Illumination for optoacoustic detection can be offered in the time or frequency domain using any of photon pulses, light of modulated intensity, chirp pulses. Preferably, illumination is offered as a pulse train with such timing characteristics so as to equivalently establish a frequency comb.

The sensor is preferably implemented in a cavity with a wide area for comfortable attachment to the skin. The geometrical characteristics of the detector serve both operational characteristics of the inventive sensor and facilitate attachment to the skin while minimizing motion artifacts. The sensor preferably establishes a surface in contact with the skin. This surface can be made of one material or be piece-wise, i.e. interrupted by a central cavity. In both cases, the surface is preferably continuous and offers an attachment characteristic so that the skin remains preferably immobile in relation to the sensor. This could be done, e.g., using a high friction surface, adhesive material, suction or other such measures. The surface can be a hard (rigid) surface or a combination of a rigid surface and a high-viscosity surface; for example as it may be implemented by filling the cavity with ultrasound gel or similar sound coupling material.

Preferably, the cavity also contributes in ultrasound signal amplification.

A preferred feature of the inventive sensor is the arrangement of enabling components within a casing. A preferred feature of the sensor is the establishment of an interface between the sensor/casing and the skin, by utilizing components and materials that are part of the casing. The interface may play various roles. One possibly important role is to establish immobility of the tissue measured (e.g. skin, endothelium, etc.) in relation to the casing and, in particular, the sensor components. Other roles relate to establishing a flat surface, useful for quantitative calculations, coupling of light and sound to/from tissue and defining the area of the measurement. Relative immobility of components is a possibly important feature of the sensor. The sensor may be utilizing a multitude of illuminating (light) sources and ultrasound detectors arranged in relation to the casing. However, as outlined above, all these components preferably establish together one interrogation volume. Therefore, the sensor preferably operates by establishing immobility between all involved moieties, i.e. the sources, detectors, casing, tissue interrogated, etc. Consequently, a measurement is preferably completed without any component or moiety moving in relation to the other. This operation is in contrast to imaging systems where a plurality of sources and/or detectors is required for detecting and separating signals from different volumes in tissue. Whereas the inventive detector can be utilized to detect in sequence signals from different locations, every measurement performed is complete by establishing immobility between all components and moieties involved.

Immobility is synonymous herein to establishing constant distances between moieties and components, i.e. immovable components in relation to each other. Since the sensor preferably has no imaging capacity, geometrical certainty is established by a rigid geometry whereby distances between components are accurately known and do not change during a measurement or from measurement to measurement. Knowing the relative distances with accuracy is then important, especially in relation to defining layers (or subsection) within the interrogation volume. This is because layers can be defined in relation to a zero geometrical point, which refers to the rigid frame of the transducer or casing. The zero geometrical point can for example be the central point on the sensor interface established, or another point defined on the sensor. Consequently, all measurements defined in the following are performed in relation to the geometrical framework defined by the sensor and this zero point of origin (ZPO) defined somewhere on the rigid structure of the sensor, e.g. the casing.

The casing preferably comprises a, preferably flat, sensing surface adapted and configured to be attached to the epidermis of a person. The one or more ultrasound detectors may be arranged at or proximate to said sensing surface. In an alternative implementation, optical and ultrasound elements are arranged along a flat surface.

The sensing surface effectively constitutes an interface between the sensor and the tissue. This interface may comprise or consist of materials that serve multiple functions. The material is preferably able to allow the propagation of acoustic (ultrasound) and optical energies, at least in the optical wavelengths and ultrasound frequencies employed. The material preferably further establishes the conditions of friction and relative tissue immobility in regard to the optical and ultrasound components. Finally the interface and corresponding material allows efficient coupling of light and sound from and to the tissue. This is particularly important for the ultrasound propagation. Allowing an air interface between the surface and tissue generates strong sound reflection which reduces the sensitivity of the sensor. Conversely, the sensing surface also ensures that no such air interface is allowed between the sensor elements and the tissue. The interface can be thought as a boundary which passes energies from the sensor to the tissue and vice versa and may consist of one continuous material or different materials preferably covering individual parts of the sensing surface. While ultrafast measurements of the sensor are possible, minimizing immobilization conditions and minimizing the importance of friction, establishment of an interface using specialized materials may also play a role of sanitation, e.g. by establishing sterile conditions, especially when measuring exposed organs and tissues (e.g. including wounds). The material can be a membrane that can be removed.

Alternatively or in addition, the casing preferably comprises an acoustic mirror adapted and configured to reflect the ultrasound signal emitted from the detection volume of the person's skin towards the one or more ultrasound detectors. Preferably, the acoustic mirror comprises a surface that defines at least a portion of a paraboloid. Preferably, the acoustic mirror comprises a surface that defines at least a portion of a rotational ellipsoid wherein a major axis of the rotational ellipsoid is preferably tilted with respect to a planar face surface of the acoustic mirror, and wherein the surface that defines at least a portion of the rotational ellipsoid is preferably recessed from the planar face surface. A focal point of the acoustic mirror is preferably arranged within or adjacent to at least one of the one or more ultrasound detectors.

Likewise the casing may contain at least one optical mirror, acoustic mirror, optical and/or acoustic waveguide and other components responsible for directing light and sound within the sensor and from/to the sensor. Moreover, optical, electrical or other cables (such as flushing lines utilized for filling sensor cavities with acoustic coupling medium such as water or gel) may run in parallel to the tissue measured. This is preferential especially in measurements performed by attachment of the sensor to the skin, since the placement of cables parallel to the skin can better support the weight of the sensor, allowing better attachment of the sensor to the skin, i.e. better establishment of immobile conditions and complete attachment of the interface to the skin.

The casing can take different forms. In handheld operations, the casing may look like a pen or a similar shape of wider dimensions, with all components placed at the tip of the pen.

Nevertheless, the preferred application as a portable sensor may assume many different shapes and placement ways, some exemplary elaborated in preferred embodiments.

The sensor preferably further comprises an optical detector. Preferably, the optical detector is encased by, preferably integrated into, the (en)casing. The optical detector may be an optical detector, single point sensor or a camera. The optical detector may use filters. Many abilities are offered by cameras or detectors, i.e in a hybrid sensor implementation combining optoacoustic and optical measurements:

The optical detector can be employed to guide positioning of the sensor in relation to the skin. The read out could be projected to a mobile device, the latter also responsible for the collection of optoacoustic and other optical measurements.

The optical detector can be used to record specific appearance of the skin for diagnostic or calibration purposes. Calibration implies a process by which imaging signals from a camera or a detector are employed within the analysis algorithms. For example by recording the skin colour, skin roughness or other characteristics and employing these characteristics to adapt an aspect of the optoacoustic signal recorded. For example multiplying the intensity of the optoacoustic signals with a factor derived in response to skin attenuation as it is optically recorded.

The optical detector can be used to derive additional diagnostic information. Preferably, the optical detector records a signal reflected from the skin surface in response to skin illumination and spectroscopically processes this information to derive aspects of skin absorption and scattering.

Preferably, the sensor utilizes a tissue-coupling machinery (adhesive, vacuum) and a coupling medium (gel, light/sound transmitting medium).

The sensor is preferably adapted and configured to perform one or more elements of the analysis discussed below. For this purpose, the sensor may comprise a processing unit adapted and configured to control the light source and/or the one or more ultrasound detectors, which processing unit is also adapted and configured to perform at least a part of the analysis discussed below. In addition or alternatively, the sensor may be part of a sensor system comprising an external device and the sensor described above having a transmission unit for transmitting the signal detected by the one or more ultrasound detectors (or an analyzed or pre-analyzed signal) to said external device. The external device may be a desktop PC, a laptop, a smartphone or another portable computing device. The external device may comprise a processor for performing part or all of the analysis discussed below. In addition or alternatively, the sensor may utilize a data analysis platform analyzing at least one of optoacoustic measurements, optical measurements, clinical tests, blood tests, -omics information, lifestyle and age parameters, other data.

One preferred aspect of the present invention relates to the processing of the data recorded. The sensor records optoacoustic data from an interrogation volume, i.e. the intersection between the volume illuminated and the field (volume) of view of the ultrasound detector(s). The sensor records data from this entire volume, however it can also separate the data recorded in sub-volumes, referred to herein as subsections or "layers", as explained in the following.

The signals recorded have preferably at least two dimensions: frequency (bandwidth) and (preferably exactly) one geometrical dimension. A third dimension can then be offered by adding illumination at multiple wavelengths and recording spectrally-dependent features (spectral features). Then, a fourth dimension can be added by adding time, i.e. performing measurements over time.

Focusing now on the first two dimensions, the geometrical dimension denotes depth from the surface of the skin, distance from the ultrasound detector or a similar measure which essentially appoints recorded data to a volume along this one geometric dimension. From an optoacoustic sense in the time domain, this dimension can be also referred to as time, i.e. the time of propagation of the ultrasound wave from different parts of the interrogated volume toward the detector. Typically this time is of the order of microseconds. However, in frequency domain implementations, i.e. implementations whereby the illuminating source has a non-ultrashort pulse waveform as in the time-domain, this dimension is independent of time; however it remains to denote an aspect of depth or distance from the detector. Therefore, we will continue referring to this dimension as the "geometrical" dimension, so as not to confuse it with the fourth time dimension which explains sensor measurements obtained at different time points in the course of disease development or of patient or individual monitoring over seconds, minutes, hours or longer time spans.

For preferably each point along the geometrical dimension, there is a certain signal collected, containing several properties, such as intensity, central frequency, bandwidth, time delay (or phase depending on the domain collected). The sensor preferably records all these parameters and later analyzes them in order to record differences between different tissues, different measurements or different layers within the interrogation volume.

The layer is employed herein to define a subsection (sub-volume) within the interrogation volume. The layer is technically defined by selecting a point or segment along the geometrical dimension and may geometrically be a flat layer, curved layer or generally the volume collected from within this point or segment of the geometrical dimension. For example, for time-domain implementations, signals are collected over time in the microsecond range.

Time relates to distance of propagation via the speed of sound in the medium. Layers can then be defined as a time segment along the signal collection axis. For a point detector these layers are spherical slices within tissue and the interrogated volume. However preferred implementations utilize elongated detectors along one or two geometrical dimensions, which then result in defining layers that may be approximately parallel to the tissue surface.

In frequency domain implementations, such layers can be defined using similar discriminations based on detecting the phase (phase delay) of the detected signal from a reference signal or similar detection measures that are equivalent to detecting time, in the time domain, via the Fourier Transform. It is to be understood that the volume interrogated can be separated in multiple layers along the geometrical dimension, or be considered as one layer. For example, assuming that the Interrogated volume spans depths from 0 mm to 3 mm under the tissue surface, we could separate the volume interrogated to one layer of 3 mm thickness, three layers of 1 mm thickness, three layers of 0.1 mm, 1 mm and 1.9 mm thickness or to 100 layers of 0.03 mm thickness. Any combination may be performed and may carry different diagnostic or other medical information. In particular, this measurement could be (and/or relate to and/or result in) one or a combination of the following features: vascular density, vascular dilatation inflammation, tissue oxygenation, metabolism/AGE's, microcirculation, lipid composition, tissue density, depth discrimination, arterial pulse-wave, elastin/collagen.

The definition of layers is a particularly advantageous feature of the inventive sensor. Conventional sensors, including optical sensors, provide one measurement of the volume interrogated. This measurement may contain contributions from multiple moieties and structures. In tissue, it could be several photo-absorbing moieties, metabolites, etc. In environmental measurements, there could be contributions from various chemicals and/or organisms. Such measurements average out contributions of each moiety and/or structure contained in the entire volume imaged. In contrast, the inventive sensor preferably utilizes the ability of optoacoustic measurements to define layers, these layers can be adaptive, as described above. Therefore, the exact sub-volume (layer) measured in the interrogated volume can be defined and adjusted dynamically, primarily by selecting a segment on the geometrical axis and a specific bandwidth measured. Focusing aspects of the ultrasound detector employed can also be utilized to offer more precise volume definition along the lateral dimension of measurement (such as depth), for example, the use of ultrasound lenses, axicons or other such ways to laterally define the field of view of the ultrasound detector. The end result is a measurement that can be obtained from a well-defined layer, in relation to the ZPO; an ability that can better differentiate constituents in smaller volumes (layers). For example, for sensing vascular alterations in the dermis, it is better to select a layer corresponding to sub-epidermis or dermis volumes and better separate signals from dermal vasculature, excluding contributions from the skin surface (epi-dermis). Likewise, metabolites or lipids distributed in the blood stream are detected with more specificity if one selects the dermal layer, vs. obtaining a measurement from the entire volume interrogated. This concept could similarly be applied to detect aspects of the epidermis or muscle by selecting more superficial or deeper positioned layers within the interrogated volume. One key advantage of this function is that contributions from different layers are not averaged together in the same measurement, therefore offering the opportunity to reject contributions from unwanted volumes and increase the precision and discrimination ability of the measurements by analyzing data from more specific volumes.

For the concept of layers discussed above it is preferred that the spatial subsections correspond to layers in relation to a well-defined geometrical reference point, i.e. a "zero geometrical point". This reference point may be a certain point with respect to the sensor or with respect to the data generated. Preferably, the processing unit is adapted and configured to automatically define this reference point on the basis of the detected ultrasound signal.

The major premise of the zero geometrical point is to definitively and quantitatively annotate a reference location by which all signals collected can be related to the exact position of the CDV scanned and layers within, in relation to the scanner. The reference location could be a point on a detector or an illuminator or the sensor casing. Due to known geometry of the sensor and the known speed of sound propagation in the coupling material of the sensor, this zero geometrical point can be then assumed not only as a point in space but also as a point in time, in particular the zero time point by which all optoacoustic measurements can be referenced to. This conversion from a point in space to a point in time and vice-versa is very advantageous to the inventive sensor, since the CDV and all the layers defined within the CDV can be precisely referenced to this geometrical point, since distance=time*(speed of sound). In other words, by means of the zero geometrical point (ZGP) we can define the exact depth at which different layers are located in tissue, computed as the distance from the ZGP. Since the ZGP is constant in relation to any other point on the sensor, simple geometrical operations (e.g. trigonometry) can then define the distance of the layers from any other point on the sensor, including a point on the surface between sensor and tissue. We note that if the coupling medium has a different speed of sound than tissue, the distance can be calculated by adding time*speed terms assuming using two speeds of sounds. Therefore the zero geometrical point (ZGP) can also help define a time zero and the exact distance of the CDV and layer within the CDV from any point in the sensor, not only the ZGP, since the distance of all points on the sensor is constant to the ZGP. As an example, the ZGP can be placed on the surface of the sensor. This could be a point under a detector or under an illuminator. By knowing the relative distance of the detector and the ZGP, simple geometrical computations and trigonometry, using the relationships distance=time*(speed of sound) can identify the time-zero point on the collected time signal. Advantageously, for a single detector, the ZGP can be placed directly on the detector and by knowing the distance of the detector from the sensor geometry define which point in time corresponds to measurements on the tissue surface, and then as a function of depth. This way information can be obtained in a quantitative manner from the first mm of tissue depth, the second mm of tissue depth etc.

In another preferential implementation, the ZGP is not assigned as a fixed point on the sensor but by utilizing a feature of the signal collected. For example, it is common that the skin generates a strong optoacoustic signal due to the presence of melanin. This information can be detected on the collected signal itself, typically seen as a strong amplitude rise. This rise can be detected by a threshold or more elaborate algorithmic method, including artificial intelligence or algorithms that detect a steep rise. Using the distance-speed conversion, this time point identified as the skin surface can be converted then to a point in space. Other signals on the optoacoustic signal can be similarly employed. Once the zero geometrical point has been defined the layers with respect to said reference point may be extracted based on time-gates applied to the raw signal, for example by registering signals arriving from 1 to 2 microseconds or 13 to 17 microseconds following the zero time point, and corresponding to certain layers within the CDV.

It is further preferred that the processing unit is adapted and configured to automatically monitor motion of skin or other tissue within the common detection volume throughout the measurement and to correct the reference point on the basis of the monitored motion. The respective algorithms for monitoring motion may in addition or alternatively be used for retrieving physiological information such as breathing and heart rate from the opto-acoustic signal. This can be for example achieved by taking the Fourier Transform of sensor data collected over time from tissue and identifying frequencies corresponding to motion or breathing or heart rate. The use of Principle Component Analysis has also been described for isolating time features on the optoacoustic signal (Opt Express (2011) 14; 19(4):3175-84. doi: 10.1364/OE.19.003175. Glatz J et al.) Furthermore, the recording and tracking of motion such as breathing or hear-rate can be utilized to correct the recorded signals for motion-induced artefacts in the data (Sci Rep. 2017; 7: 10386. doi: 10.1038/s41598-017-11277-y. Motion correction in optoacoustic mesoscopy. Schwarz et al.).

We note that the opto-acoustic signals collected have two time components that should not be confused. A "single measurement" by the sensor is a measurement over time, typically in the microsecond range, which corresponds to the propagation of optoacoustic signals from tissues to the detector. However a sensor can obtain several "single measurements" over time, for example monitoring breathing, motion or heart rate.

It is further preferred that the processing unit is adapted and configured to convert measurements, such as measurements from the entire CDV or layers from within the CDV, due to time-gating to saturation values and concentration values.

It is further preferred that the processing unit is adapted and configured to calibrate the data using, e.g., isosbestic points and the strength of the signal on the skin surface as internal reference or calibration points. For example, the skin signal may be employed to calibrate the measurements to adapt to skin color. The isosbestic points can be used, e.g., as a reference signal of total blood volume that can be used to normalize oxyhemoglobin measurement signals for saturation values, or to normalize differences between wavelengths indicative of oxy- vs. deoxy.

There are several isosbestic points in the tissue spectrum, i.e. points whereby the oxygenated and deoxygenated spectrum cross. Therefore these points are not affected by oxygenation measurements but only by total blood volume measurements. By adapting at least one wavelength to these isosbestic points (e.g. ~808 nm), the sensor could achieve two distinct advantages (J Biophotonics 2016 April; 9(4): 388-95. doi: 10.1002/jbio.201500131. Wavelength-Modulated Differential Photoacoustic Spectroscopy (WM-DPAS) for noninvasive early cancer detection and tissue hypoxia monitoring. Choi et al.). First, variations of blood volume could be directly measured. Second, this blood volume measurement can be used to calibrate oxygenation measurements. Assuming a second wavelength tuned to a peak of the oxyhemoglobin spectrum (e.g. 610 nm) and one tuned to a low point (e.g. 680 nm) collects measurements that could be combined in arithmetic operations to define oxygenation changes. For example, one can define a measurement at 610 nm minus a measurement at 680 nm and divide by a measurement at an isosbestic point in order to define a gradient of hemodynamic changes. Ideally, such metric should be first calibrated with measurements from known oxygenation states and weighted for example $M=(a*M610-b*M680)/M808$, whereby a, b are weighting factors.

More accurately however, the measurements described above, or any combination of measurements at different wavelengths could be employed in a spectral unmixing scheme, as well defined in the literature, where measurements at different wavelengths are expressed as a weighted combination (addition) of chromophore concentrations and the system of equations is solved for the unknown concentrations. Typically, the weights in these cases are the extinction coefficients of these measurements.

We also note that calibration is advantageous for accurate sensor measurements. In other words, calculation of concentrations of chromophores extracted from sensor measurements can be performed in a relative way to a reference, the latter based on calibration. We assume that a parameter recorded is signal intensity at different layers (times). This signal intensity can be a single point in time or an integral over a time period. For each wavelength, a measurement $Mln$, at wavelength $ln$, can be written as a system of equations that are a function of chromophore concentrations and extinction coefficients, i.e. $Mln=ec1[C1]+ec2[C2]+\ldots$ where $Cm$ is the mth chromophore (i.e. oxygenated hemoglobin and deoxygenated hemoglobin etc.) and $ecm$ is the corresponding extinction coefficient. However, when raw data are collected from the sensor, the measurement $Mln$ corresponds to a voltage or current and is also dependent on the strength of illumination at wavelength $ln$, therefore it is not a calibrated measurement. In order to obtain accurate measurements of the unknowns $[Cm]$, the measurements $Mln$ need to be calibrated. Calibration can happen in many different ways, for example by weighting each measurement $Mln$ with a weight factor $wln$, after a measurement from a medium with known concentrations is performed, for example from a measurement phantom (medium) acting as a standard. In the example of measuring one chromophore, $win=ec1[C1]/Mln$ for this specific measurement; but of course the measurement can be performed multiple times and for different combinations of chromophores and extract a more accurate $wln$ (also an averaged win) per $ln$. Generally, one weight is extracted per wavelength and is representative of the sensor characteristics (gain factors, losses etc) at this wavelength. However this calibration can happen also as part of the measurement itself. At least one measurement, for example a measurement at an isosbestic point, can be employed as a calibration measurement. The chromophore concentrations measured in this case can be assumed known and assigned a certain value. Then, these known concentrations can be used to calibrate the measurement, as discussed above. In particular, the sensor measurements can be first treated with pre-calculated weights from a phantom calibration, as discussed above, and then multiply all these weights with a new weight extracted from the isosbestic measurement. In this case, all concentrations extracted can be in relation to the assumed concentration at the at least one measurement. Such measurements can be employed to understand relevant concentrations, for example as they change over time.

Advantageously, the sensor can provide after calibration absolute measurements of parameters measured, i.e. vascular density, endothelial function, blood concentration, oxygen saturation etc. We note that in particular measurements of endothelial function can be performed over time, by perturbing a parameter of the tissue, for example by applying pressure to tissue, altering the temperature of tissue or reducing or stopping blood flow and then releasing the blockage and monitor recovery of those parameters. Measurements of endothelial function in particular are important for understanding the condition of the cardiovascular system. The sensor can record in these case several dynamic parameters associated with motion, heart rate, vessel elasticity etc by analyzing the rate by which the system is perturbed and the rate of tissue recovery (i.e. the signal dynamics as a function of time) and use these measurements for better understanding tissue physiological parameters and for improving the accuracy of the observation using motion correction techniques in analogy to the ones used in imaging (see also Sci Rep. 2017; 7: 10386. doi: 10.1038/s41598-017-11277-y. Motion correction in optoacoustic mesoscopy. Schwarz et al.).

It is further preferred that the processing unit is adapted and configured to convert opto-acoustic measurements to values utilizing, e.g., integration over DT, after positive filtering/other filtering, performing Fourier analysis of time segments and the like. Such processes will require for example an aspect of time gating or a filter that is applied sequentially on the time signal along time, for example a filter that operates on $1/5^{th}$ or $1/10^{th}$ or other shorter durations of the total duration of the optoacoustic signal with a middle point (time point on the optoacoustic signal whereby the filter is applied) that is moving from one point to the next of the signal, a process generally called a moving filter. For example integration or smoothing over DT is not only applied between time segments defined by hard time boundaries on the time signal but by a moving filter. Such processes are common in the signal processing literature. Likewise and importantly, Fourier analysis is not applied on a time segment of the optoacoustic signal bounded by hard time boundaries (time windowing), but on a signal processed by a moving filter to avoid the generation of artifacts. The moving filter could attenuate values outside the time segment of interest in a gradual way (apodizing) so as to not generate spurious artifacts.

The sensor preferably provides an output of at least one value which may be a combination of all signals or properties recorded from all layers, a single value recorded from a single layer or a combination of different signals from different layers. The value can be also produced as a ratio of values from different layers or different signals or properties; this process is often regarded a normalization procedure.

Usually, this selection is done through a training process of an algorithm against known standards. However this selection can be also done on a hypothesis basis, based on known pathophysiological parameters of skin. For example, the sensor reports on the bandwidth and intensity recorded from a depth of approximately 0.7-1.5 mm as representative of dermal microvasculature. The sensor detects alterations in skin microvasculature and reports them as one or multiple values. These values are then used to assess different medical conditions, e.g., the onset of diabetes and/or cardiovascular disease. Other parameters can be recorded especially with appropriate selection of one or multiple wavelengths, such as: vascular density, vascular dilatation inflammation, tissue oxygenation, metabolism/AGE's, microcirculation, lipid composition, tissue density, depth discrimination, arterial pulse-wave, elastin/collagen.

Another advantageous feature is the processing of changes of parameters measured. For example, recording of changes in oxygenated and deoxygenated hemoglobin are representative of oxygen utilization, i.e. aerobic metabolism. Therefore, the sensor can preferably report on metabolic parameters, such as oxygen utilization, lipids and lipid utilization.

Another preferential feature of the sensor is that it can utilize bandwidth measurements, in particular layer-specific bandwidth measurements to derive structural (morphological) components in tissue. Since the bandwidth recorded from each layer depends on the composition of the tissue interrogated, classification or analysis of the spectrum recorded carries information on tissue density. Moreover, observing the relative strength of different frequency components reveals information on size distribution on each layer. This is because absorbers of different sizes resonate at different ultrasound (optoacoustic) frequencies. This information may also have diagnostic, prognostic and theranostic value. These features also explain the preferred feature of utilizing broadband measurements, in order to record distributions from objects with varying sizes in tissues. For example, sensing at a few MHz corresponds to sizes of a few hundred microns. Sensing at tens of MHz corresponds to sizes of tens of microns etc. The linear relationship between size and frequency can be employed to accurately predict which size(s) of objects are recorded in each frequency or frequency window analyzed.

It is to be understood that measurements from different interrogation volumes can be accomplished by translating the sensor along the surface interrogated. Translation could be manual or based on mechanical means, for example a translation stage or a robotic-based placement. Due to intended applications to skin measurements, or from the surface of other organs, the sensor is preferably implemented in reflectance mode, i.e. both the illumination/illuminator and the detection/detector occur/are placed on the same part of a surface. This is in contrast to other applications, for example environmental applications; where the light path and ultrasound detection path may be in opposite sides of the object (trans-illumination), or along a line or at an angle to each other ranging from 180° to 45° to each other. In the reflectance mode, the relative optical and ultrasound paths may have an angle to each other but this angle can rarely exceed 120°, more practically can rarely exceed 90°. It may be also foreseen that such translation can also be implemented with using scanning components within the sensor, scanning either the illumination, ultrasound detection or both. Such translation can also be implemented by using multiple elements to establish different interrogation volumes for each element or element subgroup utilized. Nevertheless, the basis of each of these measurements is the establishment of more than one interrogation volume defined above, therefore not altering but only reproducing in space the basic inventive nature of the disclosed technology herein. Each of these measurements acts as a sensor measurement disclosed herein and they are not combined to form one image, utilizing multiple projections, as common in an imaging device.

As mentioned above, this analysis may be done by a processing unit implemented into the sensor and/or by a processing unit of an external device in communication with the sensor. In order to perform the above-mentioned analysis (or elements thereof), the processing unit is preferably adapted and configured to analyze the ultrasound signals detected, including aspects such as the intensity, time/phase of sound propagation and the bandwidth of the signal detected by the one or more ultrasound detectors in order to gain information on the distribution of absorbers of the illumination within the interrogation volume at a predetermined depth. Preferably, the processing unit is adapted and configured to record the amplitude of the signal detected by the one or more ultrasound detectors as a function of time or at different frequencies, wherein the record duration is preferably proportional to the maximum time it takes for the ultrasound signal to travel from any point within the interrogation volume to the one or more ultrasound detectors or the time required to obtain sufficient signal to noise ratio, especially when considering frequency domain implementations. Preferably, the processing unit is adapted and configured to analyze the recorded signal.

One possible method of analysis comprises dividing the recorded (or detected) signal into temporal subsections corresponding to spatial subsections of the interrogation volume at different depths. Preferably, the analysis comprises identifying one or more of the following features for one or more subsections and comparing the one or more features of one subsection with those of another subsection and/or those of the same subsection of another recording: number of minima and/or maxima, amplitudes of minima and/or maxima, relative distance between minima and/or maxima, FWHM of minima and/or maxima, signal duration, signal strength and/or phase, amplitude and/or FWHM of signal envelope. Additionally, bandwidth, central frequency, intensity profile of the frequency power spectrum and similar quantities can be recorded and analyzed. Preferably the recording of signals can be performed in the frequency domain. Alternatively, time domain signals can be treated in the frequency domain by using the Fourier transform. In this case different signals can be analyzed, including intensities in discrete frequencies, especially when using frequency comb techniques, e.g. based on pulse train illumination.

For measuring vascular density in tissue, the interrogated tissue volume is illuminated at a wavelength absorbed by hemoglobin, (e.g. 532 nm). Preferably, the illumination wavelength balances the depth required and the contrast achieved; deeper penetration possibly requiring red-shifted wavelengths (i.e. >600 nm). Based on thermoelastic expansion, vessels containing hemoglobin emit ultrasound waves with frequencies and bandwidths representative of the size of the vessel. The generated optoacoustic signals are then recorded by an ultrasound detector as a function of time or frequency. In time domain applications, the instance, at which each signal is recorded, depends on the distance of the hemoglobin carrying vasculature from the ultrasound detector, allowing for temporal segmentation of the recorded optoacoustic signal. However, analogous segmentation can occur in the frequency domain based on phase, spatial frequency and all other known representations, conversions and analysis of signals from time to frequency domains and vice versa.

By analysis of the total intensity recorded, a total vascular density parameter from the interrogated volume can be extracted. However, by analyzing the power spectrum (frequency domain), relative size distributions can be obtained by recording the intensity at different frequencies; the latter corresponding to different sizes. These analyses can be performed for the entire interrogated volume, or for layers defined within the interrogated volume. Preferentially, contributions from superficial layers (e.g. epidermis) are separated from deeper layers (e.g. dermis, muscle, or other tissue layers).

Some further considerations of this data analysis are as follows:

The amplitude of the recorded signals in the time domain gives a measure of the amount of hemoglobin (=absorber) in the vasculature and the overall tissue. Applying a windowed FFT to a number of individual consecutive layers of the recorded optoacoustic signals reveals the frequency content of the acoustic sources and reveals the size of the absorbers (the diameter of the vasculature/blood vessels) with higher frequencies corresponding to smaller vasculature and lower frequencies corresponding to bigger vasculature (this correlation is well known in the literature in optoacoustic imaging, e.g. M. Omar et al., Pushing the Optical Imaging Limits of Cancer with Multi-Frequency-Band Raster-Scan Optoacoustic Mesoscopy (RSOM), Neoplasis, vol. 17, no. 2, pp. 208-214, 2015).

Changes in the vascular system over time, or the derivative of these changes over time is indicative of blood flow/perfusion.

Analysis of pulsing variations seen in the recorded optoacoustic signals, or optical signals recorded by a hybrid implementation, can be further employed to retrieve parameters relating to heart rate.

Separation of signals from different layers enables operations that go beyond only recording the amount of vessels or vessel distribution. For example, signals from one layer (e.g.) can be employed as reference measurements to correct for example for measurements collected over time. For example, variations in the epidermis measurement over time may indicate sensor drift and may be employed to correct for such occurrence.

More elegantly, the interface established contains a standard absorber or absorber layer providing always a reference signal. This, for example, can be a sensing surface that contains a small amount of absorber so that it always presents a reliable reference measurement. This can be thought for example as an artificial melanin (absorption) layer, placed in contact with the tissue measured so as to provide reliable reference measurements. Reference measurements can be also employed to normalize other measurements in different layers, i.e. to divide other measurements so that all measurements (over time, layer, etc.) are referenced back to this reference signal for improving the accuracy, especially from measurement to measurement.

The above processes can be applied to a larger number of measurements and analysis. Referenced signals for example can be also employed in order to normalize the relative strength of illuminations at different wavelengths.

In particular, the skilled person will understand that the analysis described above may be performed in an analogous manner when measuring vascular oxygenation in tissue. However, rather than using a single illumination wavelength of e.g. 532 nm, two different illumination wavelengths (or more) are chosen to measure changes in oxygenated and deoxygenated hemoglobin. The wavelengths can be interleaved in time, as pulses, or can illuminate tissue using intensities modulated at different modulation frequencies. Then illumination can occur simultaneously. Taking advantage of the different absorption spectra of oxygenated and deoxygenated hemoglobin, and the resulting different intensity of recorded optoacoustic signals, it is possible to extract information on the oxygenation status of the vasculature (and of individual blood vessels over depth) in tissue (this is also well known in the literature, e.g. J. Biophotonics, vol. 9, no. 1-2, pp. 55-60, 2016).

For example, when using two wavelengths, an oxygen saturation measurement (in blood, tissue, etc.) can be calculated using a formula:

$$sO2 = a*R + b \qquad \text{Eq.1}$$

whereby a, b are constants typically derived through calibration using at least two measurements of different known saturations and R (ratio) is any division of any parameter measured by the sensor, preferably vascular density recorded from the same layer at the two different wavelengths.

Similarly, the selection of wavelength can separate contributions from different chromophores and agents, including melanin, fat, water, bilirubin or external agents and nanoparticles. These measurements can be employed to extract an additional number of parameters. Recording of oxygenation changes over time is representative, for example, of exercise intensity and metabolic need. Changes in vascular content are indicative of vasodilation and inflammation. Size distribution may be indicative of vessel loss. In one preferred calculation ratios of the intensity of high-frequency to the intensity of low frequency strengths recorded from the dermal layer can be used to quantify dermal vasculature loss in diabetes. Changes in lipid signal can be employed to quantify further metabolic and functional parameters, such as lipid metabolism, speed of lipid circulation in the blood stream after food intake, etc. Likewise, using mid-infrared wavelengths can be then used to sense an even larger number of parameters and metabolites, including glucose, lipids, proteins and carbohydrates based on their IR fingerprint stemming from molecular vibrational modes.

In a preferred application, the sensor is placed on top of a human (or animal) vessel, possibly with the help of optical or optoacoustic feedback, indicating for example that maximum absorption intensity is reached during the placement. The sensor can be moved around the area of a known large vessel, until a maximum signal is recorded indicating that the sensor is on top of the vessel. Then, measurements can be employed for identifying constituents and metabolites circulating in the blood stream, offering a kind of in-vivo flow cytometry. The sensor can in this case record circulatory parameters. One interesting application is to record changes in the circulation due to food intake, exercise or disease.

The ratio measurements described above are only a subset of a wider family of relevant measurements available to the sensor. Different measurements from different layers can be employed to divide or otherwise normalize a measurement. For example, high-frequency components can be referenced to a low frequency component. For example, assuming frequency comb measurements from one layer, the lowest discrete frequency recorded can be employed as reference to the other frequencies. Consequently, ratios or other normalization processes can be employed as an operation function on at least one low and at least one high frequency. For example, the ratio of the summed intensities of the 50-100 MHz frequencies over a 10 MHz frequency or the sum of the intensities of the 10-40 MHz frequencies, assuming a frequency comb at 10-100 MHz at a 10 MHz step. Ratios of time measurements and derivatives of time measurements can be similarly produced.

Preferably, the processing unit is adapted and configured to analyze the frequency content of the recorded or detected signal and/or the temporal subsections of the recorded or detected signal. Preferably, the analysis comprises transforming the recorded signal and/or parts thereof into the frequency regime and identifying one or more of the following features for one or more transformed parts and comparing the one or more features of one transformed part with those of another transformed part and/or those of the same transformed part of another recording: number of minima and/or maxima, amplitudes of minima and/or maxima, relative distance between minima and/or maxima, FWHM of minima and/or maxima, signal duration, signal strength and/or phase, amplitude and/or FWHM of signal envelope. Preferably, the parts correspond to one or more subsections and/or to parts that were previously identified in the analysis of the temporal domain.

Preferably, the processing unit is adapted and configured to identify optical absorbers within the interrogation volume, preferably to quantify the density and/or size and/or composition of the absorbers at different depths. Quantitative information regarding the identified optical absorbers may be achieved by, e.g., utilizing sliding window Fourier transformation algorithms and/or by performing Fourier transformations on temporal subsets of the detected ultrasound signal.

The sensor of the present invention preferably records opto-acoustic signals in the form of voltage amplitude over time. In preferred embodiments, the signal/data analysis may be exclusively performed by Fourier transformations (e.g., by FFT or iFFT) in the frequency domain.

For signal analysis, pre-defined sliding window Fourier transform algorithms may be applied in order to select relevant signal sections in the time domain and to subsequently perform windowed FFTs on these sections. This way, quantitative measures, e.g., about the number of absorbers with a certain size (e.g., diameter in the case of vasculature) can be obtained.

Alternatively, the acoustic signals may be selected in an interactive manner/selection, windowing ROIs (regions of interest) individually in time and applying FFTs onto each temporal section of interest. This may be done to, e.g., determine the size/diameter of the respective optical absorber/absorbers in the respective ROI.

On the basis of these results further, medically relevant data analysis can then be performed with/within the data obtained as described above: After obtaining the number of absorbers in the interrogated voxel/volume, where frequency analysis allowed for separation by size/diameter, the quantitative ratio between differently sized absorbers and absorbing structures can be determined. This way, e.g., a count (in absolute) of absorbers inside a tissue voxel/the interrogated volume can be obtained. In the case of sensing vasculature in tissue, for example, this method allows to establish an overall count of vessels sized smaller than a specific size (e.g., 50 μm), e.g. in the form of X number of absorbers sized smaller than Y.

In addition or alternatively, the ratio (relative count) between absorbers sized bigger than a specific size compared to absorbers of another specific size can be determined. In the case of sensing vasculature in tissue, for example, this method allows to establish a relative comparison between micron-sized vessels, i.e. by comparing all vessels sized between 5 and 50 μm to all vessels sized 50 and 100 μm.

In addition or alternatively, the ratio of absorber sizes can be monitored over time. In the case of sensing vasculature in tissue, for example, this can be used to measure microvascular elasticity in analogy to endothelial tonography.

Preferably, the processing unit is adapted and configured to measure one or a combination of the following parameters: density of microvasculature, subdermal tissue oxygenation saturation, dilatation of microvasculature, inflammation of skin and/or subdermal tissue, microcirculation, metabolism AGE, lipid composition, tissue density.

Preferably, the processing unit is adapted and configured to monitor and/or analyze the signal detected by the one or more ultrasound detectors over time. Preferably, the processing unit is adapted and configured to display a comparison of one or more of the parameters mentioned above over time. Preferably, the processing unit is adapted and configured to issue a warning if one or more predetermined requirements are met.

Preferably, broad-bandwidth collection and processing is performed. Broadband detection may be helpful for defining layers in a precise manner (with higher depth resolution). It may also be helpful for measuring the distribution of the sizes of different tissue optical absorbers. For example, the sensor may define different skin layers, for example epidermis, dermis, subdermis and may provide analysis of the relative distribution of absorbers, in each layer, by resolving the relative intensities of each frequency in a broadband spectrum. For example, an increase in high frequency components from one measurement to the other denotes an increase of absorbers of small size (for example venules and arterioles) in the first measurement. What is recorded however is defined by wavelength. For superficial vascular features, visible wavelengths are preferred. For characterizing lipids, measurements at wavelengths larger than 900 nm are preferred. For reaching deeper into tissue (mm to cm), wavelengths at the 650 nm-900 nm wavelength range are preferred. For reading biochemical parameters (glucose, lipids, proteins, carbohydrates), measurements in the IR and mid-IR are preferred.

Preferably, the sensor illuminates tissue at multiple wavelengths to measure both vascular and other characteristics. Measurements at different wavelengths can be separated. Frequency analysis of the frequency features can resolve tissue density parameters not available before.

The sensor of the present invention offers a number of advantages over the prior art:

The sensor defines a new sensor class yielding unique non-invasive measurements of microvascular and (patho-) physiological and other skin and other tissue parameters and constituents over depth, using single-point (single volume) broadband optoacoustic detection. Combinations with optical sensing in a hybrid format are possible that further improve the sensing ability. The inventive sensor allows for offering a mobile early warning/detection platform for cardiovascular disease, diabetes and other conditions in point of care and homebased environments. The inventive sensor goes well beyond the state of the art by merging advanced data analytics (deterministic & machine-learning) that integrate personalized information with the new class of unique skin markers measured, not available to any other non-invasive sensor today, and the potential to offer quantitative assessment of the cardiovascular status using a simple single-point, non-invasive 1 second measurement. The sensor can be used in portable, home-monitoring and wearable applications to monitor a larger number of parameters and conditions from function of healthy states (exercise, food intake, environmental, drug and other challenges), monitor for the onset of disease offering early warning and early detection, monitor for disease progression or for the evaluation of treatment efficacy. These parameters can be recorded by the sensor outputting at least one index, preferably a quantitative index that is representative of at least one condition recorded.

This index can be derived by measurements only available in the sensor measurement, sensor measurements obtained over time and other measurements and information available, including lifestyle parameters, medical history, "-omics" measurements, blood tests and other clinical tests. The index can be derived by a deterministic algorithm, for example an algorithm computing features as described above. Alternatively, the index can be derived by using training algorithms (including for example machine- or deep-learning algorithms) that combine sensor measurements and other measurements as described. Such analysis will follow published ways of analyzing information toward reaching diagnostic outputs or deriving features and indexes of conditions measured.

This algorithm and analysis can be an integral part of the sensor and enable the use of the sensor in multiple applications, from home diagnostics, exercise monitoring or mobile epidemiology studies, where distributed networks of sensors are employed to massively collect information from multiple individuals.

Accordingly, the present invention also relates to the use of a sensor described herein in a mobile early warning/detection platform for cardiovascular disease and diabetes in point of care and/or home-based environments.

The present invention further relates to a method of providing an early warning for certain diagnoses such a cardiovascular disease and/or diabetes. The method comprises providing a sensor as described herein, temporarily or permanently attaching the sensor to the epidermis of a person, illuminating (preferably repeatedly) an illumination volume within the person's skin in order to evoke an optoacoustic response and detecting the acoustic signal emitted from the detection volume of the one or more ultrasound detectors of the sensor. The method further comprises analyzing the detect signal as described herein in order to extract biomechanical and/or morphological features of the skin. Preferably, the method further comprises issuing a warning if one or more of the extracted biomechanical and/or morphological features meets one or more predetermined requirements.

It is expected that the inventive sensor, in the long run, will substitute DOS/NIRS sensors altogether. The inventive sensor generalizes tissue measurements far beyond pulse oximetry and arterial wave sensors, offering accuracy and wealth of measurements never before available to optical sensing. Nevertheless, through hybrid implementations, the sensor can combine its inventive abilities for extraction of tissue features or establishment of indexes with abilities of optical sensors.

Further preferred aspects of the inventive sensor are enumerated below:

1. A sensor for non-invasive optoacoustic measurements of features of skin and/or other tissue, in particular of biomechanical and/or morphological features of skin and/or other tissue, the sensor comprising:

a casing adapted and configured to be attached to the epidermis of a person;

a light source adapted and configured to, preferably simultaneously, illuminate an illumination volume of the person's skin tissue once the casing is attached to the epidermis of the person; and one or more ultrasound detectors adapted and configured to detect an ultrasound signal emitted from a, preferably common, detection volume of the person's skin and/or other tissue once the casing is attached to the epidermis of the person, wherein the intersection between the illumination volume and the common detection volume defines an interrogation volume and wherein the interrogation volume is preferably well-defined and preferably remains fixed once the casing is attached to the epidermis of the person.

2. The sensor of aspect 1, wherein the light source and/or the one or more ultrasound detectors remain stationary during detection.

3. The sensor of aspect 1 or aspect 2, wherein the sensor is adapted and configured to collect data from the entire interrogation volume and to geometrically discriminate data originating from subsections of the interrogation volume having different distances from the one or more ultrasound detectors.

4. The sensor of aspect 3, wherein the sensor is not adapted to geometrically discriminate data originating from subsections of the interrogation volume having the same distance from the one or more ultrasound detectors.

5. The sensor of aspect 3 or aspect 4, wherein the sensor is adapted and configured to analyze data originating from one or more specific subsections of the interrogation volume having different distances from the one or more ultrasound detectors and to extract biomechanical and/or morphological features of the skin and/or other tissue at different depths.

6. The sensor of any one of the preceding aspects, wherein the interrogation volume has a size of at least 500.000 $\mu m^3$, preferably of at least 0.001 $mm^3$, more preferably of at least 0.002 $mm^3$, even more preferably of at least 0.004 $mm^3$ and most preferably of at least 0.01 $mm^3$.

7. The sensor of any one of the preceding aspects, wherein the casing comprises a, preferably flat, sensing surface adapted and configured to be attached to the epidermis of a person and wherein the interrogation volume has a maximum cross section substantially parallel to said sensing surface being at least 7.500 $\mu m^2$, preferably at least 15.000 $\mu m^2$, more preferably at least 30.000 $\mu m^2$ and most preferably at least 60.000 $\mu m^2$.

8. The sensor of any one of the preceding aspects, wherein the casing comprises a, preferably flat, sensing surface adapted and configured to be attached to the epidermis of a person and wherein the interrogation volume has a maximum extension substantially perpendicular to said sensing surface being at least 100 $\mu m$, preferably at least 200 $\mu m$, more preferably at least 300 $\mu m$ and most preferably at least 500 $\mu m$.

9. The sensor of any one of the preceding aspects, wherein the one or more ultrasound detectors are broadband detectors adapted and configured to detect ultrasound over a frequency band of at least 30 MHz, preferably at least 50 MHz, more preferably at least 70 MHz.

10. The sensor of any one of the preceding aspects, wherein the one or more ultrasound detectors are broadband detectors adapted and configured to detect ultrasound over a frequency band covering at least 20-40 MHz, preferably at least 15-60 MHz, more preferably at least 10-80 MHz.

11. The sensor of any one of the preceding aspects, wherein the light source comprises a laser and/or an LED and/or wherein said light source is an intensity modulated light source or a pulsed light source.

12. The sensor of any one of the preceding aspects, further comprising an optical detector.

13. The sensor of aspect 12, wherein the optical detector is encased by, preferably integrated into, the casing.

14. The sensor of any one of the preceding aspects, wherein the casing comprises a, preferably flat, sensing surface adapted and configured to be attached to the epidermis of a person and wherein the one or more ultrasound detectors are arranged at or proximate to said sensing surface.

15. The sensor of any one of aspects 1 to 13, wherein the casing comprises an acoustic mirror adapted and configured to reflect the ultrasound signal emitted from the detection volume of the person's skin towards the one or more ultrasound detectors.

16. The sensor of aspect 15, wherein the acoustic mirror comprises a surface that defines at least a portion of a paraboloid.

17. The sensor of aspect 15, wherein the acoustic mirror comprises a surface that defines at least a portion of a rotational ellipsoid, wherein a major axis of the rotational ellipsoid is preferably tilted with respect to a planar face surface of the acoustic mirror, and wherein the surface that defines at least a portion of the rotational ellipsoid is preferably recessed from the planar face surface.

18. The sensor of any one of aspects 15 to 17, wherein a focal point of the acoustic mirror is arranged within or adjacent to at least one of the one or more ultrasound detectors.

19. The sensor of any one of the preceding aspects, wherein the sensor comprises a processing unit adapted and configured to control the light source and/or the one or more ultrasound detectors.

20. The sensor of aspect 19, wherein the processing unit is adapted and configured to analyze the time of sound propagation and the bandwidth of the signal detected by the one or more ultrasound detectors in order to gain information on the distribution of absorbers of the illumination within the interrogation volume of the person's skin at a predetermined depth.

21. The sensor of aspect 19 or 20, wherein the processing unit is adapted and configured to record the amplitude of the signal detected by the one or more ultrasound detectors as a function of time, wherein the record duration is preferably proportional to the maximum time it takes for the ultrasound signal to travel from any point within the interrogation volume to the one or more ultrasound detectors.

22. The sensor of aspect 21, wherein the processing unit is adapted and configured to analyze the recorded signal.

23. The sensor of aspect 22, wherein the analysis comprises dividing the recorded signal into temporal subsections corresponding to spatial subsections of the interrogation volume at different depths.

24. The sensor of aspect 23, wherein the analysis comprises identifying one or more of the following features for one or more subsections and comparing the one or more features of one subsection with those of another subsection and/or those of the same subsection of another recording: number of minima and/or maxima, amplitudes of minima and/or maxima, relative distance between minima and/or maxima, FWHM of minima and/or maxima, signal duration, signal strength and/or phase, amplitude and/or FWHM of signal envelope.

25. The sensor of any of aspects 21 to 24, wherein the processing unit is adapted and configured to analyze the frequency content of the recorded signal and/or the temporal subsections of the recorded signal.

26. The sensor of aspect 25, wherein the analysis comprises transforming the recorded signal and/or parts thereof into the frequency regime and identifying one or more of the following features for one or more transformed parts and comparing the one or more features of one transformed part with those of another transformed part and/or those of the same transformed part of another recording: number of minima and/or maxima, amplitudes of minima and/or maxima, relative distance between minima and/or maxima, FWHM of minima and/or maxima, signal duration, signal strength and/or phase, amplitude and/or FWHM of signal envelope.

27. The sensor of aspect 26, wherein the parts correspond to one or more subsections and/or to parts that were previously identified in the analysis of the temporal domain.

28. The sensor of any of aspects 21 to 27, wherein the processing unit is adapted and configured to identify optical absorbers within the interrogation volume, preferably to quantify the density and/or size and/or composition of the absorbers at different depths.

29. The sensor of any of aspects 19 to 28, wherein the processing unit is adapted and configured to measure one or a combination of the following parameters: density of microvasculature, subdermal tissue oxygenation saturation, dilatation of microvasculature, inflammation of skin and/or subdermal tissue, microcirculation, metabolism AGE, lipid composition, tissue density.

30. The sensor system of any of aspects 19 to 29, wherein the processing unit is adapted and configured to monitor and/or analyze the signal detected by the one or more ultrasound detectors over time.

31. The sensor of aspect 30, wherein the processing unit is adapted and configured to display a comparison of one or more of the parameters according to aspect 29 over time.

32. The sensor of aspect 30 or 31, wherein the processing unit is adapted and configured to issue a warning if one or more predetermined requirements are met.

33. The sensor of any of aspects 19 to 32, wherein the biochemical and morphological features comprise one or a combination of: Vascular Density, Vascular Dilatation.

Inflammation, Tissue Oxygenation, Metabolism/AGE's (Glucose), Microcirculation of blood, Lipid composition, Tissue Density, Depth discrimination, Arterial pulse waves, Elastin and Collagen.

34. The sensor of any one of the preceding aspects, wherein a detection radius is in the range of 0.5-1 mm.

35. The sensor of any one of the preceding aspects, wherein sensor has a curved geometry with a wide area in order to comfortably attach to the skin and collect measurements of high accuracy.

36. The sensor of any one of the preceding aspects, wherein the optical detector is a camera guiding placement of the sensor in areas of interest, wherein guidance can be adjusted to different features depending on the wavelength utilized.

37. The sensor of any one of the preceding aspects, wherein the sensor is adapted to analyse measurements as a function of depth, frequency, illumination wavelength(s), combination of readings from different detectors and external data from other measurements or assessments, including measurements from the optical sensor (pulse oximetry, arterial waveforms).

38. The sensor of any one of the preceding aspects, wherein the sensor is suitable for static measurements assessing parameters of the skin and/or other tissue and/or the cardio vascular system.

39. The sensor of any one of the preceding aspects, wherein the sensor is suitable for longitudinal measurements and adapted to establish a personalized timeline upon which it detects persistent changes indicative of disease onset or progression.

40. The sensor of any one of the preceding aspects, wherein the sensor is utilized in point of care of homebased environments.

41. The sensor of any one of the preceding aspects, wherein the sensor can be used for quantifying disease readings.

42. The sensor of any one of the preceding aspects, wherein the sensor can be used as an early warning or early detection of disease.

43. The sensor of any one of the preceding aspects, wherein data from the sensor can be combined with Machine Learning algorithms to identify key features of different diseases.

44. The sensor of any one of the preceding aspects, wherein data from the sensor can be combined with Machine Learning algorithms to produce a disease detector, in particular early detection or disease burden quantification, in particular as it applies to monitoring disease prevention or treatment.

45. The sensor of any one of the preceding aspects, wherein the illumination is pulsed illumination or light of modulated intensity.

46. The sensor of any one of the preceding aspects, wherein the illumination is pulse train illumination, preferably using Golay modes.

47. The sensor of any one of the preceding aspects, wherein the detection is performed with an ADC and processed in a computer unit.

48. The sensor of any one of the preceding aspects, wherein data are transmitted to a collection device, wherein data from multiple sensors can be centrally collected for processing and meta-analysis.

49. The sensor of any one of the preceding aspects, wherein sensor data central processing may be combined with other measurements and data available to deliver prediction models and mobile epidemiology.

50. The sensor of any one of the preceding aspects, wherein the sensor is implemented within/around an acoustic cavity for ultrasound amplification.

51. The sensor of any one of the preceding aspects, wherein the sensor is implemented with 300 MHz bandwidth using an optical interferometer, characterizing an advanced number of density features.

52. The sensor of any one of the preceding aspects, wherein the sensor is implemented with at least two wavelengths for oxygenation measurements.

53. The sensor of any one of the preceding aspects, wherein the sensor utilizes frequency to gain quantification of different depths.

54. The sensor of any one of the preceding aspects, wherein the sensor utilizes algorithms for disease classification based on any of the data analysed.

Figure 1A:
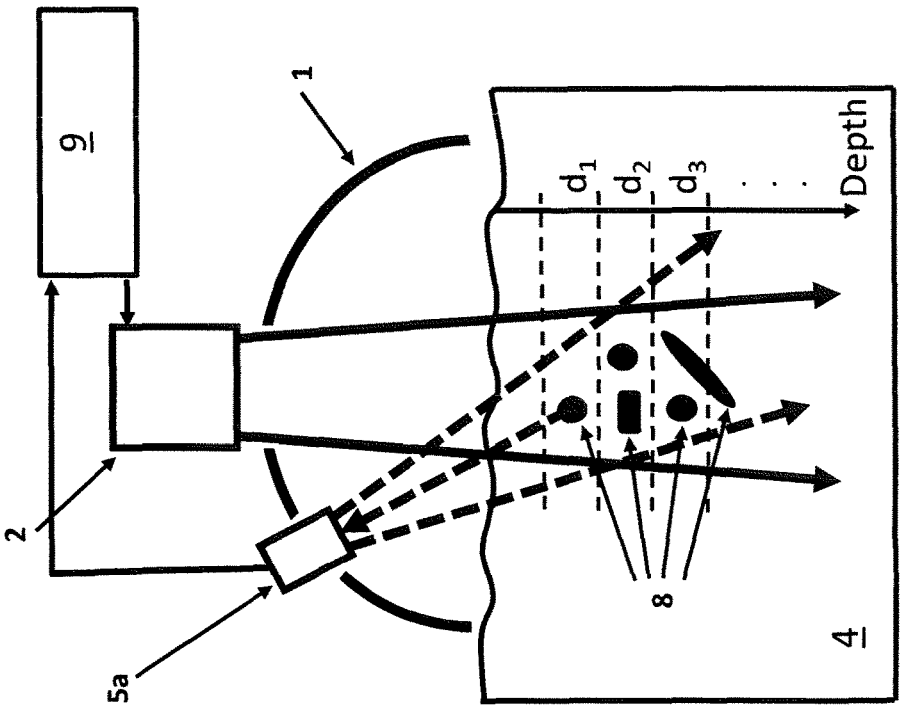
Figure 2:
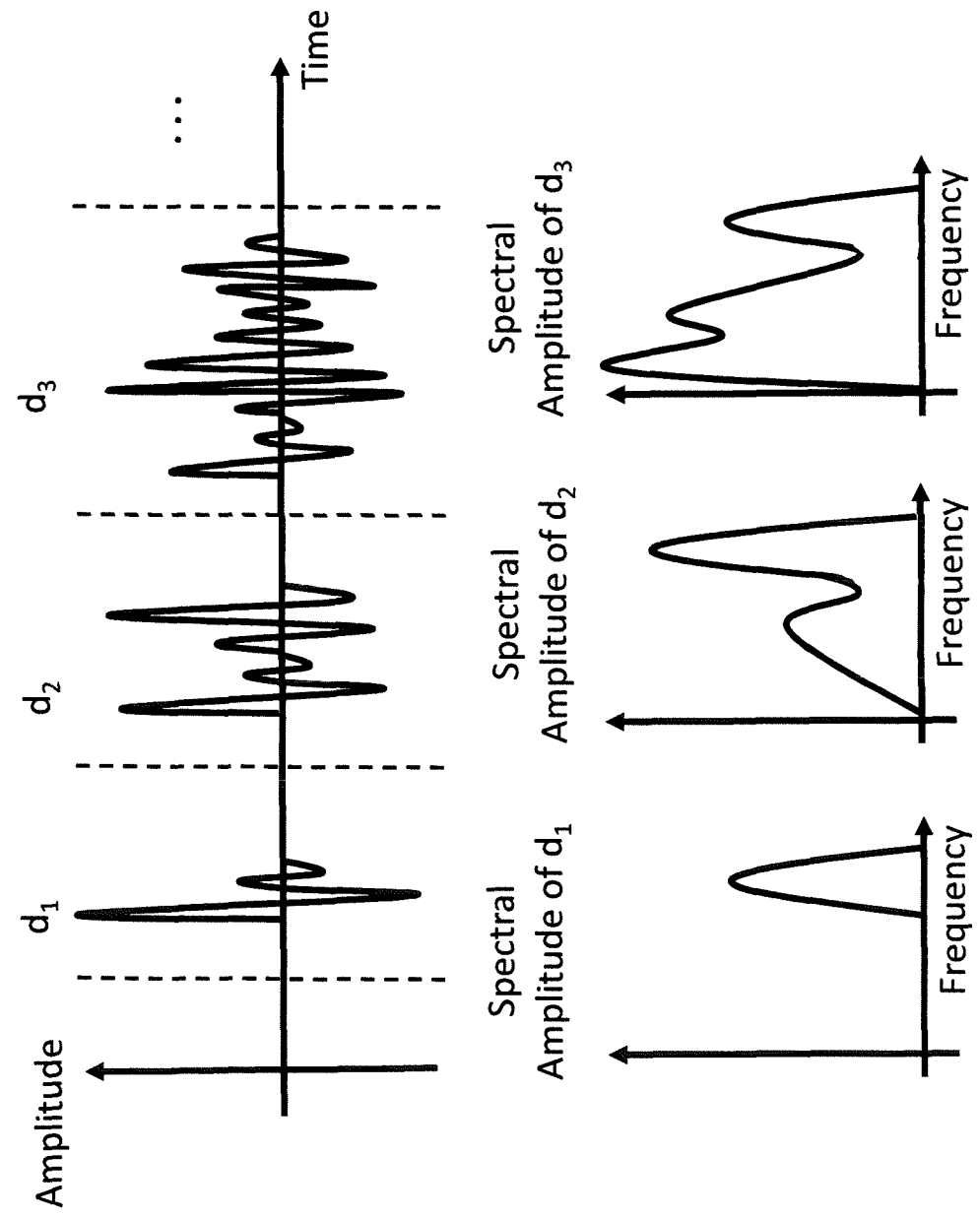
Figure 3A:
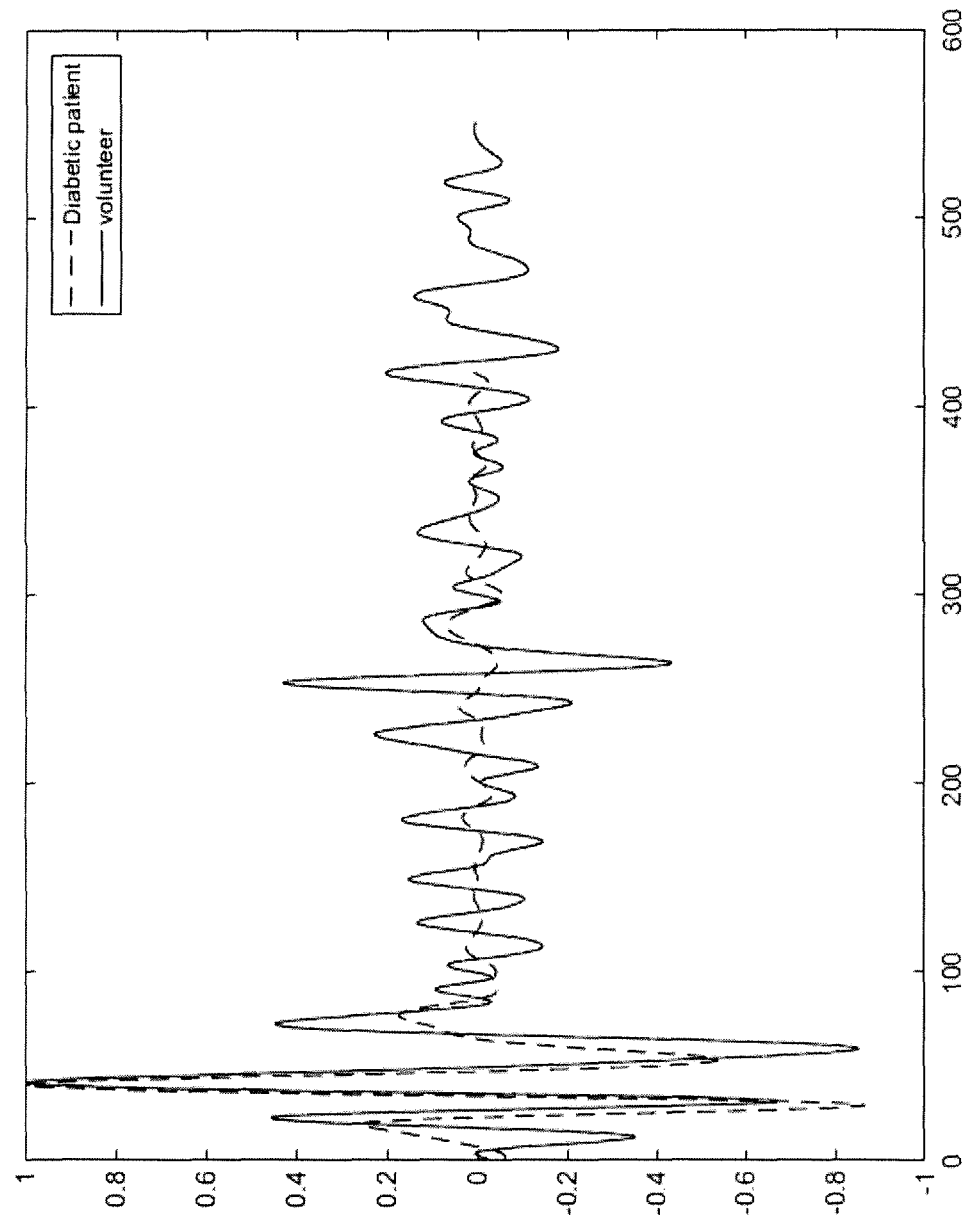
Figure 3B:
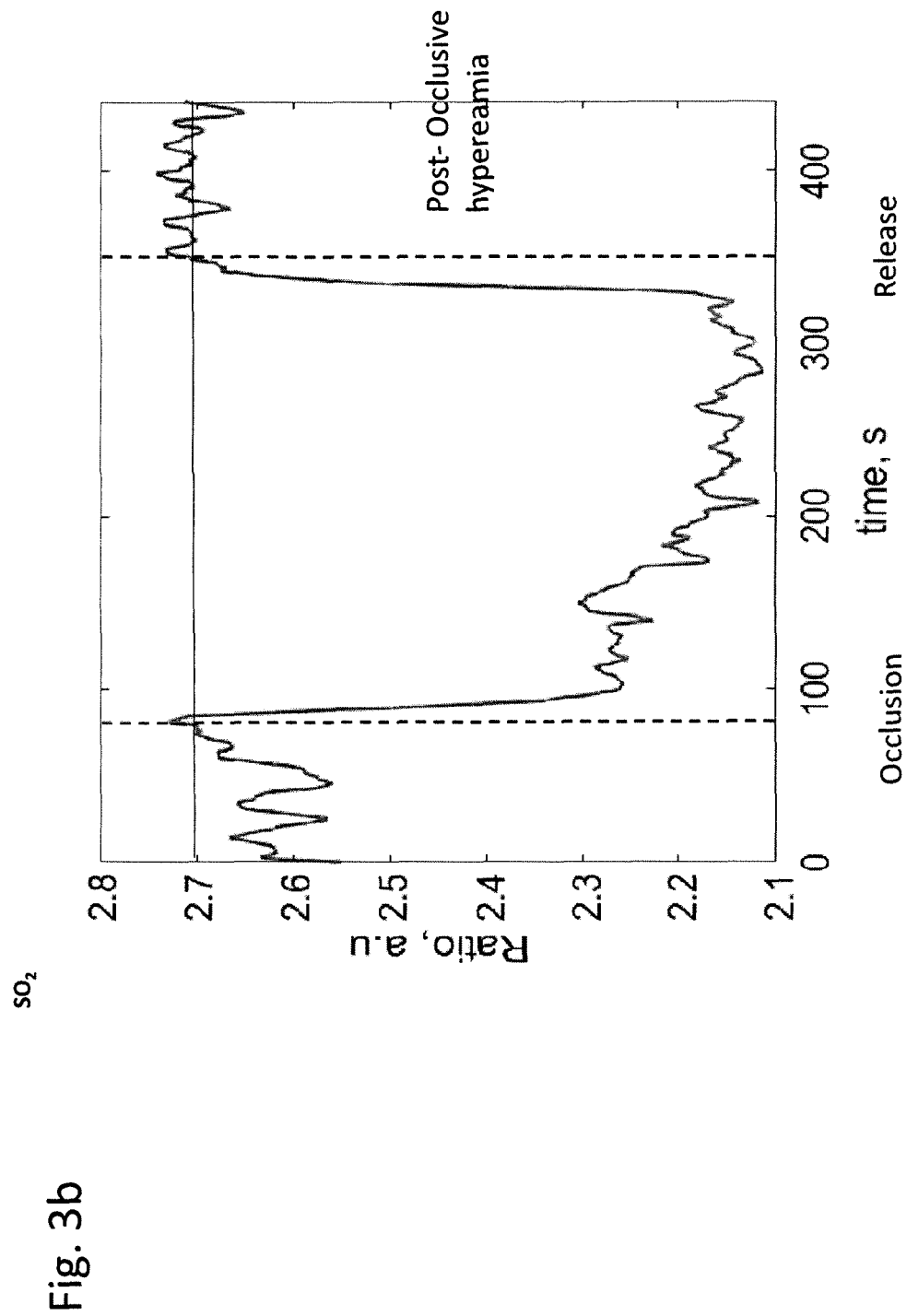
Figure 4A:
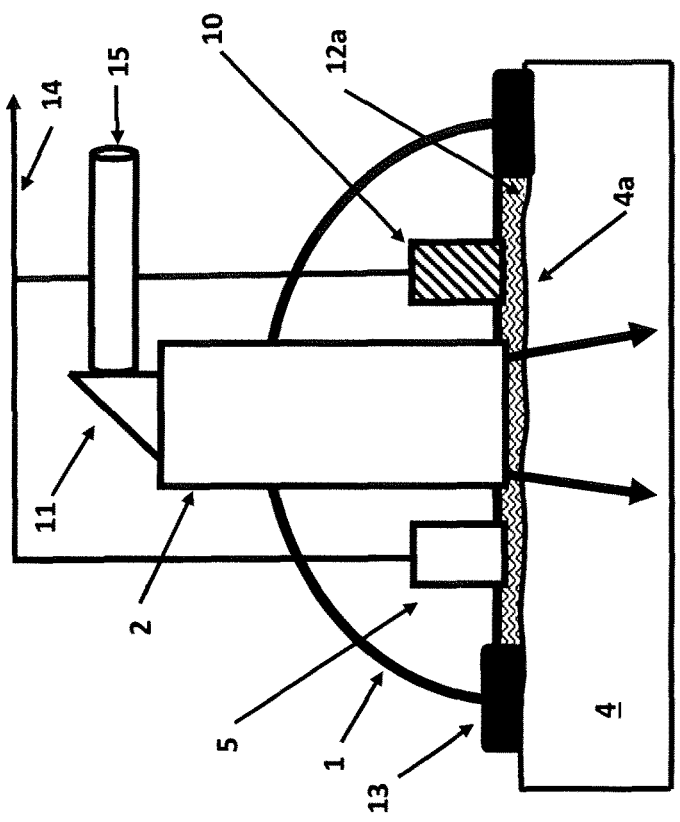
Figure 4B:
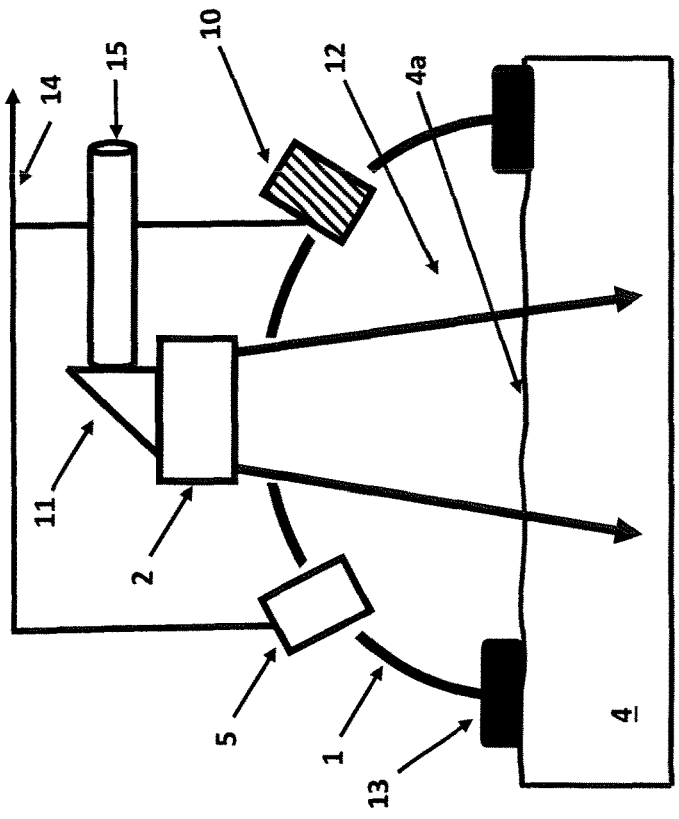
Figure 6:
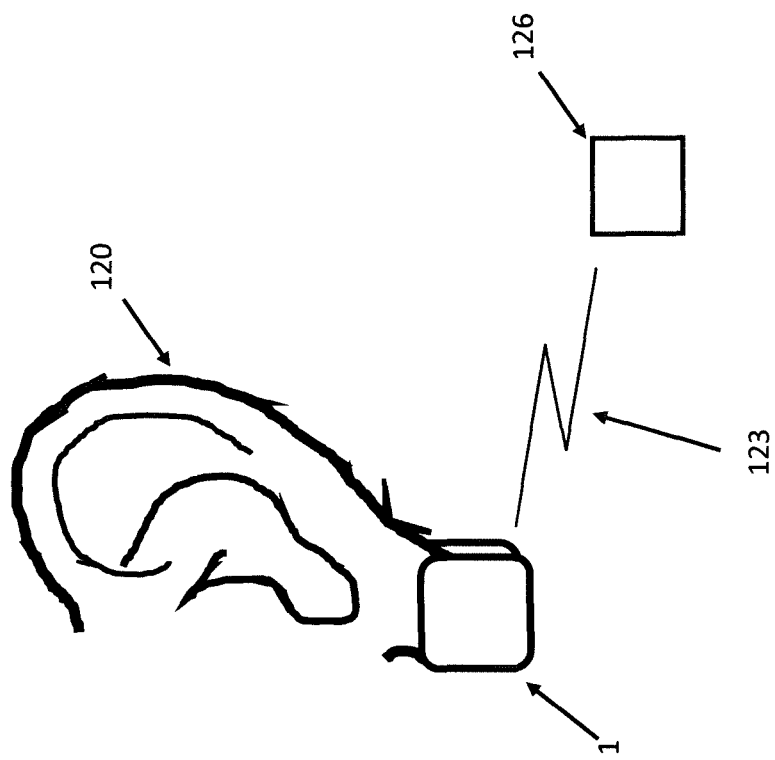
Figure 5:
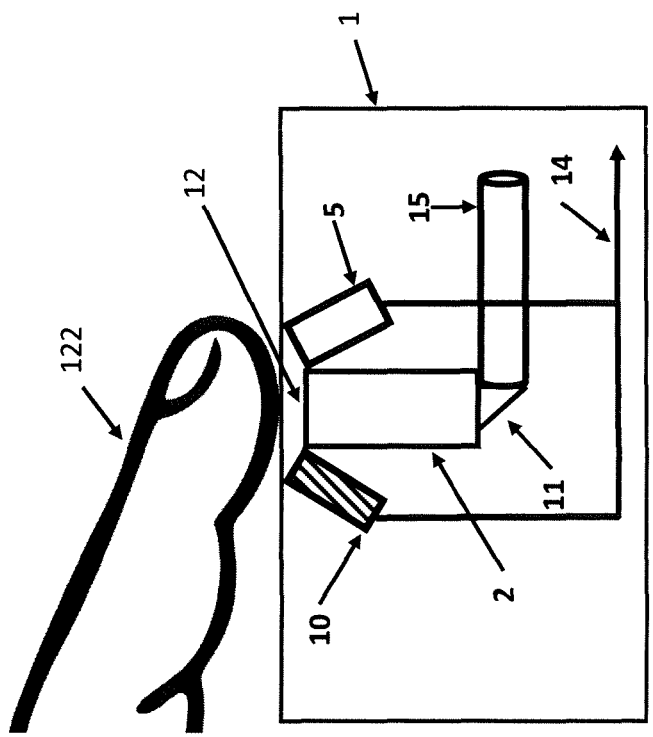
Figure 7B:
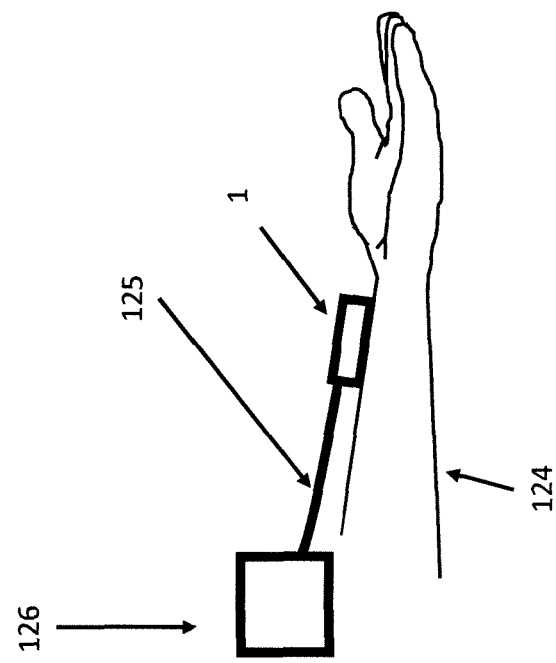
Figure 7A:
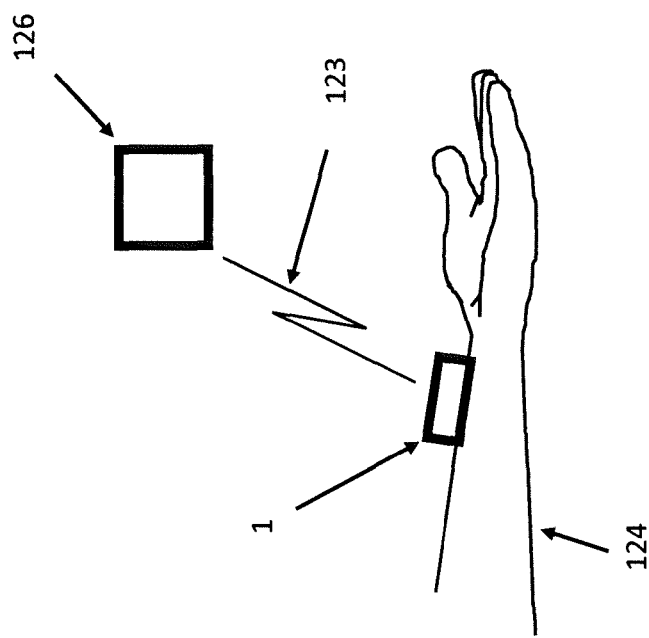

Preferred embodiments are described below with reference to the following figures which show:

FIG. 1a: schematically a preferred embodiment of a sensor according to the present invention;

FIG. 1b: schematically another preferred embodiment of a sensor according to the present invention;

FIG. 2: schematically signals detected by a sensor according to a preferred embodiment;

FIG. 3a: an exemplary microvascular signal from a healthy volunteer and a diabetic patient;

FIG. 3b: an exemplary functional test of a subdermal microvasculature (oxygenation change);

FIG. 4a: a preferred embodiment of a sensor according to the present invention;

FIG. 4b: another preferred embodiment of a sensor according to the present invention;

FIG. 5: a schematic view illustrating an exemplary use of the sensor according to a preferred embodiment;

FIG. 6: a schematic view illustrating an exemplary use of the sensor according to a preferred embodiment;

FIG. 7a: a schematic view illustrating an exemplary use of the sensor according to a preferred embodiment with wireless data transmission;

FIG. 7b: a schematic view illustrating an exemplary use of the sensor according to a preferred embodiment with wired data transmission.

FIGS. 1a and 1b schematically show two preferred embodiments of a sensor for non-invasive optoacoustic measurements of biomechanical and/or morphological features of skin tissue according to the present invention. The sensor comprises a casing 1 adapted and configured to be attached to the epidermis of skin tissue 4 of a person. The casing 1 may also define an acoustic chamber, i.e. an acoustic mirror adapted and configured to reflect the ultrasound signal emitted from the acoustic absorbers 8 of the skin tissue 4 towards the ultrasound detector 5a, 5b. For this purpose, it is particularly preferably to mount the ultrasound detector 5b at or close to a focal point of the acoustic mirror (which may have the shape if a paraboloid or a rotational ellipsoid) as indicated in FIG. 1b. The sensor further comprises a light source 2 adapted and configured to simultaneously illuminate an illumination volume of the person's skin tissue 4. The sensor further comprises one or more ultrasound detectors 5a, 5b adapted and configured to detect an ultrasound signal (schematically indicated as a dashed line in FIGS. 1a and 1b) emitted from a common detection volume of the person's skin tissue 4. The sensor further comprises a processing unit 9 adapted and configured to control the light source 2 and the ultrasound detector 5a, 5b. The processing unit 9 may comprise one or a combination of a data acquisition unit, a control unit, and a display unit.

As mentioned previously, the invention is, inter alia, based on the idea to gather all information from a single interrogation volume which is defined by the intersection between the illumination volume and the single common detection volume of the one or more ultrasound detectors (one of which is shown in FIGS. 1a and 1b), which remains stationary during detection, i.e. during the non-invasive optoacoustic measurement, and to extract certain biomechanical and/or morphological features of the skin tissue within said interrogation volume by analyzing the information collected from said single interrogation volume. In case of FIG. 1a, the illumination volume has a cone-like shape and is schematically indicated by two solid lines originating from the light source 2. Similarly, the detection volume of the ultrasound detector 5a has a cone-like shape and is schematically indicated by two dashed lines originating from the ultrasound detector 5a. The intersection of these two three-dimensional cone-like shapes defines the interrogation volume of the inventive sensor.

In case of FIG. 1b, the illumination volume also has a cone-like shape and is schematically indicated by two solid lines originating from the light source 2. However, the detection volume of the ultrasound detector 5b, due to the acoustic mirror 1, has a hyperbolic shape and is schematically indicated by two dashed lines originating from the acoustic mirror 1. The intersection of these two three-dimensional shapes defines the interrogation volume of the inventive sensor. In this context, it is to be noted that neither the illumination volume nor the detection volume infinitely extends further downwards. Rather, as mentioned above, the illumination volume, in the context of the present invention, is defined as the volume comprising all points in space where the intensity of illumination corresponds to at least 50% of the maximum illumination, and the detection volume, in the context of the present invention, is defined as the volume comprising all points in space where the sensitivity of the one or more ultrasound detectors corresponds to at least 50% of the maximum sensitivity.

Since the illumination volume is illuminated simultaneously (not taking the velocity of light into account) and since the interrogation volume remains fixed once the casing is attached to the epidermis of the person, the sensor according to the present invention eliminates the need for scanning and, in particular, for any moving parts within the sensor. This allows for a much more simple and less costly technical implementation than prior imaging devices, because the light source 2 and the one or more ultrasound detectors 5a, 5b (as well as the acoustic mirror 1) preferably remain stationary with respect to each other during detection and, accordingly, can be implemented as immovable parts within the sensor casing.

Preferably, the processing unit 9 is adapted and configured to analyze the time of sound propagation and the bandwidth of the signal detected by the ultrasound detector 5a, 5b in order to gain information on the distribution of the acoustic absorbers 8 of the illumination within the interrogation volume of the person's skin 4 at a predetermined depth. FIGS. 1a and 1b schematically show three different subsections or "layers" at different depths $d_1$, $d_2$ and $d_3$.

FIG. 2 schematically shows a typical signal detected by the detector 5a, 5b shown in FIGS. 1a and 1b. The signal may, for example, comprise a signal amplitude versus time. As may be taken from FIG. 2, the three layers or subsections identified in FIGS. 1a and 1b may be attributed to different time intervals of the detected or recorded signal. Consequently, the processing unit 9 is adapted and configured to extract certain portions of the detected or recorded signal and to attribute a spectral amplitude to each of the three layers shown in FIGS. 1a and 1b (see top of FIG. 2). Similarly, a frequency response may be attributed to each layer in the frequency domain (see bottom of FIG. 2).

The signals detected by the sensor according to the present invention and the analysis performed by its processing unit may be utilized for various diagnostic measurements. For example, FIG. 3a shows the microvascular signal of a patient having diabetes in comparison to that of a healthy person versus depth in micrometer. In particular, FIG. 3a shows the microvasculature density (vascular plexus) for different depths. Since the time of sound propagation encodes depth, whereby the bandwidth of the ultrasound wave carries information on the distribution of absorbers in each depth and offers depth discrimination, the inventive sensor allows for extracting the microvascular density for different depths.

For measuring vascular density in tissue, the interrogated tissue volume is illuminated by a pulsed laser (with a wavelength of, e.g., 532 nm, where hemoglobin has an optical absorption peak). Upon absorption, hemoglobin in the vasculature experiences a temperature increase followed by a thermal expansion, in turn generating an ultrasonic pressure wave in the surrounding medium (which is commonly referred to as optoacoustic signal). The generated optoacoustic signals are then recorded by an ultrasound detector over time. Here, the instance at which each signal is recorded, depends on the distance of the hemoglobin carrying vasculature from the ultrasound detector, allowing for temporal segmentation of the recorded optoacoustic signal stream. Each segment of the signal stream contains information relating to the vasculature from a tissue layer that is defined such that each segment of it is located at the same distance from the ultrasound detector.

By analysis of each temporal segment, it is possible to extract a measure of the overall amount and the size of the vasculature and individual blood vessels as a function of depth (equals distance from the ultrasound detector) in the interrogated volume. The amplitude of the recorded signals in the time domain gives a measure about the amount of hemoglobin (=absorber) in the vasculature and the overall tissue. Applying a windowed FFT to a number of individual consecutive layers of the recorded optoacoustic signals reveals the frequency content of the acoustic sources and reveals the size of the absorber (the diameter of the vasculature/blood vessels) with higher frequencies corresponding to smaller vasculature and lower frequencies corresponding to bigger vasculature (this correlation is well known in the literature in optoacoustic imaging, e.g., M. Omar et al., Pushing the Optical Imaging Limits of Cancer with Multi-Frequency-Band Raster-Scan Optoacoustic Mesoscopy (RSOM), Neoplasis, vol. 17, no. 2, pp. 208-214, 2015).

As may be taken from FIG. 3a, the microvascular signal is much more pronounced in case of the healthy volunteer as compared to the diabetes patient. This is particularly true for depths beyond about 100 µm.

FIG. 3b shows a functional test of tissue/vascular plexus subdermal oxygenation from a human finger during baseline, occlusion and release.

The skilled person will understand that the analysis described above for measuring vascular density in tissue may be performed in an analogous manner when measuring vascular oxygenation in tissue. However, rather than using a single illumination wavelength of, e.g., 532 nm, two different illumination wavelengths are chosen to match the oxygenated and deoxygenated hemoglobin as absorbers in the tissue's vasculature in a succeeding manner. Taking advantage of the different absorption spectra of oxygenated and deoxygenated hemoglobin and the resulting different intensities of recorded optoacoustic signals, it is possible to extract information on the oxygenation status of the vasculature (and of individual blood vessels over depth) in tissue (this is also well known in the literature, e.g. M. Schwarz et al., Three-dimensional multispectral optoacoustic mesoscopy reveals melanin and blood oxygenation in human skin in vivo, J. Biophotonics, vol. 9, no. 1-2, pp. 55-60, 2016).

As may be taken from FIG. 3b, occlusion and release are clearly visible in the detected signal.

FIGS. 4a and 4b show two further preferred embodiments of a sensor for non-invasive optoacoustic measurements of biomechanical and/or morphological features of skin tissue. The sensor of both FIGS. 4a and 4b comprises a casing 1, a light source 2 and an ultrasound detector 5. The casing 1 is adapted and configured to be attached to the epidermis 4a of skin 4 of a person by means of a skin attachment 13. In the preferred embodiments shown, light is guided through a fiber optic cable 15 through an optical port 11 to the light source 2. Moreover, a power and communication cable 14 is attached to the sensor and connected to a respective port (not shown) at or within the casing 1. An optional optical detector 10 is also shown.

In case of FIG. 4a, the casing 1 defines an acoustic mirror adapted and configured to reflect the ultrasound signal emitted from the skin 4 towards the two ultrasound detector 5. For this purpose, the acoustic mirror 1 preferably comprises a surface that defines at least a portion of a rotational ellipsoid, wherein a major axis of the rotational ellipsoid is preferably tilted with respect to a planar face surface of the acoustic mirror and wherein the surface that defines at least a portion of the rotational ellipsoid is preferably recessed from the planar face surface.

Moreover, a focal point of the acoustic mirror 1 is preferably arranged within or adjacent to the ultrasound detector 5.

In the embodiments shown in FIG. 4b, no such acoustic mirror is present and both the ultrasound detector 5 and the optical detector 10 are arranged adjacent to the light source 2 and adjacent to the tissue 4. Preferably, the ultrasound detector 5 is in direct contact with the epidermis 4a by means of a coupling gel 12a. In order to improve coupling in case of the embodiment shown in FIG. 4a, the acoustic cavity formed by the acoustic mirror 1 may be filled with a coupling medium 12.

FIG. 5 depicts the schematic working principle of an exemplary embodiment of the inventive sensor (such as that shown, e.g., in FIG. 4a). The sensor comprises a casing 1 forming an acoustic cavity filled with a coupling medium 12, an ultrasound detector 5, an optical light source 2 and optionally an optical detector 10. The light is guided through a fiber optic cable 15 and through an optical port 11. The sensor is embodied in the casing in a way to allow to extract, e.g., biomechanical and/or morphological information of tissue and vasculature in skin when sliding a finger 122 over it. The ultrasound detector 10 is in contact with the finger 122 through the coupling medium 12 and the optical light source 2 illuminates the finger 122 through the coupling medium 12. A power and communication cable 14 is connected to an external port (not shown) to connect to a data collection and data processing device.

FIG. 6 depicts the schematic working principle of another exemplary embodiment of the inventive sensor (such as that shown, e.g., in FIG. 4b). The casing 1 comprises, e.g., the sensor elements discussed above with respect to FIG. 4b and may incorporate every element (not shown) necessary for the generation and detection of optoacoustic signals in the ear lobe 120 as well as optical detectors (not shown). The data collection and data analysis is performed in a device 126 and data communication might be performed via a communication cable (not shown) or via a wireless data connection 123. The wireless data connection 123 might be a Bluetooth, WiFi or similar established wireless data transmission standard. The casing 1 of the sensor according to this embodiment can be attached to the ear (lobe) 120 by a suitable attachment mechanism such as a clip or the like and allows to extract, e.g., biomechanical and/or morphological information from the tissue in the ear (lobe) 120.

FIG. 7a and FIG. 7b show two further schematics of preferred working principles of the sensor according to the present invention. The casing 1 of the sensor is, in this example, attached to the forearm 124 to extract biomechanical and morphological information from the tissue in the forearm 124. In case of FIG. 7a, data communication between the sensor and an external device is performed via a wireless data connection 123. In case of FIG. 7b, data communication is performed via a wired data connection 125. The data collection and data analysis is performed in the device 126 similar to the one shown in FIG. 6.

In an advantageous application of the sensor, the sensor is attached to the epidermis of a person and measurements are obtained from the interrogation volume consisting of a number of wavelengths, exemplary three wavelengths at 532 nm, 580 nm and 930 nm. The measurements take approximately one second. The illumination comprises an ultrafast photon pulse in the time domain. Then the sensor is removed from the epidermis. The recorded data are separated into different layers, exemplary three layers, the epidermis, dermis and underlying muscle, by selecting the appropriate time segments in the ultrasound signal recorded, approximately corresponding to the three tissue layers, as known for human dimensions. The measurements for each layer and each wavelength are Fourier transformed. The ultrafast photon pulse lasts, e.g., 3 nanoseconds. This generates a frequency response that is broader than 10-100 MHz. Frequencies are grouped together into 5 bands, i.e. 10-30, 30-50, 50-70, 70-90, and 90-110 MHz. This generates a data set of 3 layers×3 wavelengths×5 spectral bands=45 measurements. The sensor and processing unit may use these 45 measurements in any combination and as part of any function, such as ratios, linear fits, subtraction and any other mathematical operation and algorithmic processing, in order to derive at least one value, also termed herein an index, indicative of at least one feature of tissue. For example the sensor can analyze the relative intensities of high frequency bands in the dermal layer, in order to output a value of vascular density. Or take the ratio of vascular densities in different wavelengths to calculate dermal oxygenation.

The sensor in the above example can take measurements over 10 time points, possibly corresponding to 10 different tissue states over this time span. For example physiological changes as a function of exercise within seconds or minutes, effects of a drug on vasculature or lipid concentration in muscle within days or disease progression within months and years. The measurement then contains 450 measurements. These measurements are again amenable to any mathematical operation in order to extract at least one value, including time and spatial gradients; spatial gradients understood along the geometrical dimension and indicating changes between tissue layers. Some of these measurements can be utilized for reference or data normalization purposes.

This exemplary description of 45 or 450 measurements can contain any measurement from 1 to thousands or more. Nevertheless, deterministic analyses, discussed above can be substituted by more elaborate data analysis methods, using training data sets for algorithmic adjustment and calibration or training of machine learning algorithms, that can treat all data as a whole and not as individualized measurements. Therefore even if layers are conceptually included in the measurement, everything collected by the sensor can be processed as one signal.

When information is taken from predetermined structures, for example blood vessels, wounds, fingernails, eyes, skin lesions, then specific information about these structures and lesions can be obtained, that is not restricted to vasculature measurements but can generally refer to a number of different moieties, including lipids, water, melanin, circulating particles and constituents, labelled viruses and other biological moieties, collagen, bilirubin, cytochrome oxidase, advanced glycolysis end-products (AGE's), food or other constituents in circulation or distributing in the extra-cellular space, etc. Detection specificity could be improved in this case by utilizing a larger number of wavelengths, utilizing classification techniques for data collected or employing machine learning and artificial intelligence techniques. For application in diabetes detection and progression monitoring, measurements at the extremities may be preferred.

This information can be rendered as numbers or as a line of values, possible color-coded, and representing one or more parameters for each layer.

In a second advantageous example, the pulse train illumination has a tighter timing between pulses compared to the time domain, i.e. termed herein pulse-train illumination, resulting in the generation of a number of discrete frequencies, i.e. using the same pulse-train/frequency comb implementation. For example while time-domain pulse trains utilize pulses of 1-10 nanoseconds at KHz repetition rates, pulse-train illumination for generating a frequency comb can assume characteristics of pulses emitted in the MHz range, for example 1-10 Mhz using 25 ns pulses. In this case the measurement may consist of a millisecond-long train of nanosecond pulses generated by a laser diode or an LED. This method has been understood to provide better signal to noise ratio characteristics than conventional time-domain illuminations. The theory of frequency comb generation is well established in the literature. Another main difference over time domain is that signals can be detected as the amplitude and phase of discrete frequencies directly in the frequency domain in this case. This operation essentially records spatial frequency along the line of the geometrical dimension, for example it records 10 frequencies at 10, 20, 30, . . . , 100 MHz, which correspond to the spatial frequencies contained in the interrogation volume, along the geometrical dimension. These frequencies recorded can also be grouped together generating windows of say 10-30 MHz, 30-50 MHz etc. Due to the known linear equivalency between time and frequency domains, the data recorded can be taken in the time domain or processed directly in the frequency to define layers along the geometrical dimension; the analysis being then equivalent to the one described above for the time-domain data collection. Advantageously, data can be treated however directly in the frequency domain or treated as raw data of amplitude and phase using classification or machine learning techniques.

For example classification can utilize any of the information collected in the above implementations to classify a measurement based on features (properties) contained in the measurement to a parameter or index representative of a desired function, for example for early diagnosis, identifying disease, for quantifying disease progression, for quantifying lipid content or oxygenation state as a function of time etc.

The invention claimed is:

1. A sensor for non-invasive optoacoustic measurements of features of skin or other tissue, the sensor comprising:
   a casing adapted and configured to be attached to the epidermis of a person; a light source adapted and configured to simultaneously illuminate an illumination volume of the skin or other tissue once the casing is attached to the epidermis of the person;
   one or more ultrasound detectors adapted and configured to detect an ultrasound signal emitted from a common detection volume of the skin or other tissue once the casing is attached to the epidermis of the person, wherein an intersection between the illumination volume and the common detection volume defines an interrogation volume that remains fixed once the casing is attached to the epidermis of the person; and
   a processing unit adapted and configured to control the light source and/or the one or more ultrasound detectors, wherein the processing unit is adapted and configured to record the ultrasound signal detected by the one or more ultrasound detectors as a function of time, wherein the processing unit is adapted and configured to analyze the recorded ultrasound signal and wherein said analysis comprises dividing the recorded ultrasound signal into temporal subsections corresponding to different layers of the interrogation volume at different depths, attributing the different layers to different temporal subsections, and using the recorded ultrasound signal of a one of the temporal subsections to modify the recorded ultrasound signal of another one of the temporal subsections.

2. The sensor of claim 1, wherein the light source and/or the one or more ultrasound detectors remain stationary in relation to each other during detection.

3. The sensor of claim 1, wherein the sensor is adapted and configured to collect data from the entire interrogation volume and to discriminate data originating from the different layers of the interrogation volume having different distances from the one or more ultrasound detectors.

4. The sensor of claim 3, wherein the sensor is not adapted to geometrically discriminate data originating from the different layers of the interrogation volume having the same distance from the one or more ultrasound detectors.

5. The sensor of claim 3, wherein the sensor is adapted and configured to analyze data originating from one or more specific ones of the different layers of the interrogation volume having different distances from the one or more ultrasound detectors and to extract biomechanical and/or morphological and/or physiological and/or molecular features of the skin and/or other tissue at different depths.

6. The sensor of claim 1, wherein the one or more ultrasound detectors are broadband detectors adapted and configured to detect ultrasound over a frequency band of at least 30 MHz.

7. The sensor of claim 1, wherein a duration of the recorded ultrasound signal is proportional to a maximum time it takes for the recorded ultrasound signal to travel from any point within the interrogation volume to the one or more ultrasound detectors.

8. The sensor of claim 1, wherein the analysis comprises identifying one or more of the following features for one or more of the different layers and comparing the one or more features of one of the different layers with those of another one of the different layers and/or those of the same one of the different layers of another recorded ultrasound signal: number of minima and/or maxima, amplitudes of minima and/or maxima, relative distance between minima and/or maxima, FWHM of minima and/or maxima, signal duration, signal strength and/or phase, amplitude and/or FWHM of signal envelope.

9. The sensor of claim 1, wherein the processing unit is adapted and configured to analyze a frequency content of the recorded ultrasound signal and/or the temporal subsections of the recorded ultrasound signal.

10. The sensor of claim 9, wherein the analysis comprises transforming the recorded ultrasound signal and/or parts thereof into a frequency regime and identifying one or more of the following features for one or more transformed parts and comparing the one or more features of one of the one or more transformed parts with those of another of the one or more transformed parts and/or those of the same one of the one or more transformed parts of another recorded ultrasound signal: number of minima and/or maxima, amplitudes of minima and/or maxima, relative distance between minima and/or maxima, FWHM of minima and/or maxima, signal duration, signal strength and/or phase, amplitude and/or FWHM of signal envelope.

11. The sensor of claim 10, wherein the one or more transformed parts correspond to one or more of the different layers and/or to parts that were previously identified in the analysis of the recorded ultrasound signal.

12. The sensor of claim 1, wherein the processing unit is adapted and configured to identify optical absorbers within the interrogation volume.

13. The sensor of claim 12, wherein quantitative information regarding the identified optical absorbers is achieved by utilizing sliding window Fourier transformation algorithms and/or by performing Fourier transformations on temporal subsets of the recorded detected ultrasound signal.

14. The sensor of claim 12, wherein the processing unit is adapted and configured to quantify a density and/or size and/or composition of the optical absorbers at different depths.

15. The sensor of claim 1, wherein the casing comprises an acoustic mirror adapted and configured to reflect the ultrasound signal emitted from the detection volume of the skin or other tissue towards the one or more ultrasound detectors.

16. The sensor of claim 15, wherein the acoustic mirror comprises a surface that defines at least a portion of a paraboloid.

17. The sensor of claim 15, wherein the acoustic mirror comprises a surface that defines at least a portion of a rotational ellipsoid.

18. The sensor of claim 17, wherein a major axis of the rotational ellipsoid is tilted with respect to a planar face surface of the acoustic mirror.

19. The sensor of claim 18, wherein a surface that defines at least a portion of the rotational ellipsoid is recessed from the planar face surface.

20. The sensor of claim 15, wherein a focal point of the acoustic mirror is arranged within or adjacent to at least one of the one or more ultrasound detectors.

21. The sensor of claim 1, wherein the processing unit is adapted and configured to measure one or a combination of the following parameters: density of microvasculature, subdermal tissue oxygenation saturation, dilatation of microvasculature, inflammation of skin and/or subdermal tissue, microcirculation, metabolism AGE, lipid composition, tissue density.

22. The sensor of claim 1, wherein the different layers correspond to layers in relation to a well-defined geometrical reference point.

23. The sensor of claim 22, wherein the processing unit is adapted and configured to automatically define the geometrical reference point on the basis of the recorded ultrasound signal.

24. The sensor of claim 22, wherein the processing unit is adapted and configured to automatically monitor motion of skin or other tissue within the common detection volume and to correct the reference point on the basis of the monitored motion.

25. The sensor of claim 1, further comprising an optical detector or a camera configured for obtaining an image of a portion of the illumination volume.

26. The sensor of claim 1, wherein the analysis further comprises individually analyzing a plurality of the temporal subsections.

27. The sensor of claim 1, wherein the analysis further comprises analyzing at least one of the temporal subsections to measure vascular density of the attributed one of the different layers.

* * * * *